United States Patent
Tu et al.

(10) Patent No.: US 6,969,367 B2
(45) Date of Patent: Nov. 29, 2005

(54) EXTRACORPOREAL PATHOGEN REDUCTION SYSTEM

(75) Inventors: Hosheng Tu, Newport Beach, CA (US); Hun-Chi Lin, Los Angeles, CA (US); Yu-An Chang, Irvine, CA (US)

(73) Assignee: XEPMED, Inc., Los Angeles, CA (US)

( * ) Notice: Subject to any disclaimer, the term of this patent is extended or adjusted under 35 U.S.C. 154(b) by 105 days.

(21) Appl. No.: 10/720,811

(22) Filed: Nov. 24, 2003

(65) Prior Publication Data

US 2005/0059921 A1 Mar. 17, 2005

Related U.S. Application Data

(63) Continuation-in-part of application No. 10/195,814, filed on Jul. 15, 2002, which is a continuation-in-part of application No. 09/496,613, filed on Feb. 2, 2000, now Pat. No. 6,423,023.

(60) Provisional application No. 60/429,126, filed on Nov. 26, 2002, provisional application No. 60/494,895, filed on Aug. 13, 2003.

(51) Int. Cl.$^7$ .......... A61M 37/00; C02F 1/44; B01D 33/00; C07K 1/00
(52) U.S. Cl. .......... 604/6.04; 604/6.09; 604/6.08; 210/359; 210/385; 210/780; 210/645; 210/321.75; 435/269
(58) Field of Search .......... 604/4.01, 5.01, 604/5.04, 6.04, 6.08, 6.09, 6.11, 6.06, 6.16, 604/28, 20, 7–10; 210/637, 651, 247, 780–2, 210/209, 297, 321.87, 645, 385, 359, 314, 210/316, 321.84, 600, 634, 641, 194, 195.1; 422/44; 435/173.3, 262, 267, 269; 600/1, 600/2

(56) References Cited

U.S. PATENT DOCUMENTS

| | | |
|---|---|---|
| 3,705,100 A | 12/1972 | Blatt et al. |
| 4,191,182 A | 3/1980 | Popovich et al. |
| 4,735,726 A | 4/1988 | Duggins |
| 4,737,140 A * | 4/1988 | Lee et al. .......... 604/6.08 |
| 4,895,558 A | 1/1990 | Cham |
| 5,034,135 A | 7/1991 | Fischel |
| 5,194,145 A | 3/1993 | Schoendorfer |
| 5,234,608 A | 8/1993 | Duff |
| 5,376,263 A | 12/1994 | Fischel |
| 5,419,759 A | 5/1995 | Naficy |
| 5,484,396 A | 1/1996 | Naficy |
| 5,529,691 A | 6/1996 | Brown |
| 5,971,948 A | 10/1999 | Pages et al. |
| 6,099,734 A | 8/2000 | Boggs et al. |
| 6,194,395 B1 | 2/2001 | Schultz et al. |
| 6,194,430 B1 | 2/2001 | Camden et al. |
| 6,219,584 B1 * | 4/2001 | Lee .......... 700/90 |
| RE37,584 E | 3/2002 | Cham |
| 6,423,023 B1 | 7/2002 | Chang et al. |
| 6,548,241 B1 | 4/2003 | McBurney et al. |
| 6,642,008 B1 | 11/2003 | Harley et al. |
| 2002/0004030 A1 | 1/2002 | Ericsson |
| 2002/0043051 A1* | 4/2002 | Manica et al. .......... 53/469 |
| 2002/0095108 A1* | 7/2002 | Tsuchida et al. .......... 604/6.08 |
| 2003/0186213 A1 | 10/2003 | McBurney et al. |

* cited by examiner

*Primary Examiner*—Patricia Bianco
*Assistant Examiner*—Leslie Deak

(57) ABSTRACT

The invention relates to an apparatus system and methods for treatment of virus-infected or pathogen-loaded human blood components separated from normal components comprising a separation apparatus and treatment apparatus system that inactivate pathogens in an extracorporeal body fluid system.

17 Claims, 9 Drawing Sheets

Within the broken lines (- - -) is a separation chamber arrangement

EXTRACORPOREAL PATHOGEN REDUCTION SYSTEM

RELATIONSHIP TO COPENDING APPLICATIONS

This patent application is a continuation-in-part application of Ser. No. 10/195,814, filed Jul. 15, 2002 entitled "Methods and Apparatus for Enhanced Apheresis", which is a continuation-in-part application of Ser. No. 09/496,613, filed Feb. 2, 2000, entitled "Method and Apparatus for Enhanced Plasmapheresis", now U.S. Pat. No. 6,423,023, both of which are incorporated herein by reference in their entireties. The application also claims priority benefits of provisional application Ser. No. 60/429,126, filed Nov. 26, 2002 and provisional application Ser. No. 60/494,895, filed Aug. 13, 2003, entire contents of which are incorporated herein by reference.

TECHNICAL FIELD OF THE INVENTION

The present invention generally relates to medical apparatus and methods for treating plasma or blood infected with virus. More particularly, the invention relates to an apparatus system and methods for treatment of virus-infected human blood components separated from normal components comprising a separation apparatus and treatment apparatus system that inactivate pathogens in an extracorporeal cell-free body fluid system.

BACKGROUND OF THE INVENTION

Blood Components Separation

Separation of blood into a plasma fraction and a cellular component fraction is desirable for many medical reasons. For example, separation of blood into plasma fractions and cellular component fractions provides for a collection of plasma alone, with the cellular component being returned to the donor with an optionally suitable portion of replacement fluid. Thus, continuous plasmapheresis provides for the collection of plasma from donors without the removal of the cellular components of the blood. Plasma donation from a patient or donor is generally allowed about twice a week whereas the whole blood donation is allowed once in every two months. Secondly, continuous plasmapheresis can be used therapeutically to remove pathologic substances contained in the plasma portion of the blood, as disclosed by Popovich et al. in U.S. Pat. No. 4,191,182. This can be accomplished by separating the cellular components from the diseased plasma and returning the cellular components to the patient in admixture with a suitable replacement fluid, or by further fractionating the patient's plasma to remove the unwanted substances and returning a major portion of the patient's plasma with the cellular components.

The separation of blood into cellular component fractions and plasma fractions has inherently some difficulties and complications. A brief discussion of the makeup of blood is shown herein for illustration purposes. Approximately 45% of the volume of blood is in the form of cellular components. These cellular components include red cells, white cells and platelets. If cellular components are not handled correctly, the cells may lose their functionality and become useless. Plasma makes up the remaining 55% of the volume of blood. Basically, plasma is the fluid portion of the blood which suspends the cells and comprises a solution of approximately 90% water, 7% protein and 3% of various other organic and inorganic solutes. As used herein, the term "plasmapheresis" refers to the separation of a portion of the plasma fraction of the blood from the cellular components thereof.

Ultrafiltration has been widely used on a batch-type or continuous basis as a substitute for, or in combination with, dialysis methods in artificial kidneys and the like. In any plasmapheresis-type process effected by ultrafiltration there are various problems which occur during the fractionating of the blood by passing it in a parallel flow pattern over a membrane surface, with a transmembrane pressure sufficient to push the plasma portion of the blood therethrough, while allowing the cellular component portion of the blood to remain thereon. One of these problems is that the flow rates must be controlled fairly closely. Thus, if the flow rate employed is too fast at any moment or at any specific region, detrimental turbulence may occur and excess shear force may cause unwanted hemolysis resulting in general destruction of cellular components. On the other hand, if the flow rate and the transmembrane pressure are not controlled adequately the cellular and macromolecular components of the blood will tend to clog up the membrane thus significantly slowing the ultrafiltration rate. Such clogging can also cause hemolysis to occur.

Along the blood flow route in a plasmapheresis apparatus, plasma continues to pass through the filter membrane while cellular component remains in the blood stream. At the downstream region of the separation process, the blood becomes more viscous and the separation efficiency decreases drastically. This fouling effect or "concentration polarization" phenomenon becomes obvious in a conventional batch-wise or continuous ultrafiltration process. For example, U.S. Pat. No. 3,705,100 to Blatt et al., issued on Dec. 5, 1972, discloses a process and apparatus for a blood fractionating process on a batch basis. Furthermore, U.S. Pat. No. 4,191,182 to Popovich et al., issued Mar. 4, 1980, discloses means for continuous plasmapheresis including blood input pumping means and plasma outflow pumping means. Though the average flow rate of the disclosed device is within the non-hemolysis range, the local flow rate and its shear force at any moment and/or at any specific region of the filter membrane may not be adequate to effect the most efficient plasmapheresis. Concentration polarization usually occurs at a later stage in a batch plasmapheresis or at a downstream region in a continuous plasmapheresis.

To alleviate the concentration polarization drawbacks, Solomon et al. in U.S. Pat. No. 4,212,742 discloses a filtration device employing a microporous filtration membrane. The filtration flow channels along the surface of the upstream side of the membrane wall are provided with gradually and uniformly increases from the inlet end to the outlet end of the flow channel, whereby the membrane wall shear force of the suspension in laminar flow through the flow channel gradually and uniformly varies along the length of the flow channel from a maximum value at its inlet end to a minimum value at its outlet end. There are complex issues in designing and operating such a unit. Further, Solomon et al. device requires enormous membrane surfaces for blood plasma separation which appear not economically practical.

For the purposes of increasing the transmembrane pressure drop hopefully to catch a higher separation efficiency and a less concentration polarization effect, Fischel in U.S. Pat. No. 5,034,135, Schoendorfer in U.S. Pat. No. 5,194,145, Duff in U.S. Pat. No. 5,234,608, Fischel in U.S. Pat. No. 5,376,263, and Brown in U.S. Pat. No. 5,529,691 all disclose a blood separating system comprising high rotational velocity flow applying centrifugal forces aiming for added transmembrane pressure drop. During high centrifugal rotation, a portion of the cellular components may undesirably remain in the rotational device or inside pores of the filter membrane for a prolonged time and may subject to hemolysis, cellular damage or membrane clogging. For centrifugal-type separation processes, the local shear force for the cellular components of the blood concentrate fraction is the highest at about the outermost periphery of the separation apparatus, such as a spinner-type device and the like. The requirement of a proper shear force at the outermost region in a rotational separator apparently limits the size, and therefore the capacity, of the separation apparatus or the spinner. The centrifuge-type separation apparatus also generally suffers concentration polarization disadvantages.

Alternately, to create adequate local flow rate and subsequently local shear force in a plasmapheresis process, Duggins in U.S. Pat. No. 4,735,726 discloses a process for continuous plasmapheresis comprising conducting blood over a microporous membrane in a reciprocatory pulsatile flow pattern. The pulsatile flow is known to cause certain degrees of turbulence as the pulsatile flow rate changes constantly which may possibly cause cell damage and membrane clogging. Duggins discloses a damage-controlling method to compensate for the shortcomings of the pulsatile flow in a continuous plasmapheresis by reducing the transmembrane pressure difference to below zero during each forward and reverse flow. This additional equipment setup and control mechanism for repetitively reversing the transmembrane pressure difference makes this process less economically attractive.

Virus Infection

AIDS (acquired immuno-deficiency syndrome) is one of the leading causes of death for Americans between the ages of 25 and 44. HIV (human immunodeficiency virus) is the virus most researchers believe causes AIDS. The virus exists in the blood circulation of a patient in two forms. One form is as cell-free virus or mature virion having a lipid envelope, and the other is as cell-associated virus or replicating virus in the infected cells. According to the Center for Disease Control (CDC), the definition of AIDS includes two factors: HIV positive and CD4 (T-cell) count below 200 or presence of one or more opportunistic infections. About 47 million people worldwide have been infected with HIV since the start of the epidemic.

The virus attacks the immune system and leaves the body vulnerable to a variety of life-threatening illnesses and cancers. Common bacteria, yeast, parasites, and viruses that ordinarily do not cause serious disease in people with fully functional immune systems can cause fatal illnesses in people with AIDS. According to the teachings in U.S. Pat. No. 5,419,759, the full-blown AIDS is characterized by weight loss, fever, severe headache, neck stiffness, arthralgia, and skin rash. The virus is essentially an intracellular parasite and in order to survive and perpetuate itself it has to penetrate and infect the host cells. The lipid envelope with its glycoprotein spikes provides the means for penetrating and infecting the white cells. The virus replicates inside the infected cells and produces mature virions with lipid envelope and glycoprotein spikes, budding from the membrane of the infected cell. These mature virions in turn penetrate and infect the new and healthy cells as they are released from the hematopoietic system, and the vicious cycle goes on.

T-cells (or T-lymphocytes) are white blood cells that play important roles in the immune system. There are two main types of T-cells. One type has molecules called CD4 on its surface. These "helper" cells orchestrate the body's response to certain microorganisms such as viruses. The other T-cells, which have a molecule called CD8, destroy cells that are infected and produce antiviral substances. The target host cells invaded by HIV known today include CD4 T-lymphocytes, monocytes, macrophages and colorectal cells.

HIV is able to attach itself to the CD4 molecule, allowing the virus to enter and infect these cells. Even while a person with HIV feels well and has no symptoms, billions of CD4 T-cells are infected by HIV and are destroyed each day and billions more CD4 T-cells are produced to replace them.

Other sexually transmitted diseases may include human papilloma virus and hepatitis B virus, which are associated with cervical carcinoma and hepatocellular carcinoma, respectively.

Separation of Virus-Infected Blood Components

Naficy in U.S. Pat. No. 5,419,759 and U.S. Pat. No. 5,484,396, the entire contents of both being incorporated herein by reference, discloses that the HIV is an enveloped virus having lipids in its outer envelope. Naficy also discloses using diethyl ether to dissolve or destroy the lipid envelope of HIV, thereby destroying the glycoprotein spikes and rendering the virus unable to penetrate and infect the healthy cells. Earlier, Cham in U.S. Pat. No. 4,895,558, entire contents of which are incroporated herein by reference, discloses a method for autologous plasma delipidation of an animal using a continuous flow system with means to delipidate the plasma using a lipid solvent, wherein the preferred solvent is di-isopropyl ether.

Cham in U.S. Pat. No. RE37,584, entire contents of which are incorporated herein by reference, discloses a solvent extraction method for de-virusing plasma, wherein the suitable solvents may comprise mixtures of hydrocarbons, ethers and alcohols. Though it is known in the prior art that alcohol, ether, hydrocarbons, or combination thereof is feasible in de-virusing the plasma, none of the above-cited prior art discloses a separation apparatus and methods under an orbital motion that has optimal local shear forces and desired quality flow output for the intended HIV delipidation therapy.

Hildreth in U.S. patent application Publication No. 2002/0128227 and Publication 2002/0132791, entire contents of which are incorporated herein by reference, discloses: methods of reducing the risk of transmission of a sexually transmitted pathogen by contacting the pathogen or cells susceptible to infection by the pathogen with a beta-cyclodextrin; methods for reducing the risk of transmission of a sexually transmitted pathogen to or from a subject by contacting the pathogen or cells susceptible to the pathogen in the subject with a pharmaceutical composition containing a beta-cyclodextrin.

To reduce the risk of transmission of a sexually transmitted pathogen to or from a subject is important. However, to treat the subject already infected with a sexually transmitted pathogen becomes equally or even more important. Hildreth fails to disclose a method or system for treating a patient infected with the sexually transmitted pathogen or cells susceptible to the pathogen to extend the patient's quality of life.

McBurney et al. in U.S. Pat. No. 6,548,241 and U.S. patent application Publication No. 2003/0186213, the entire contents of both being incorporated herein by reference, disclose a platelet/additive solution comprising bicarbonate, citrate, glucose and a photosensitizer for inactivating pathogens. One embodiment is to place the solution with a photosensitizer, preferably 7,8-dimethyl-10-ribityl-isalloxazine, in a photopermeable container such as a blood bag and agitated while exposing to photoradiation.

Therefore, there is an unmet clinical need to provide an effective and economical plasmapheresis and de-virus processes in an extracorporeal pathogen reduction system by minimizing the cellular damage while increasing the quality flow output for reinfusion purposes. This may be achievable by controlling the local flow rate and local shear force of an apparatus system comprising an orbital motion to minimize or eliminate problems of undesired turbulence, concentration polarization, or incomplete liquid-liquid mixing encountered in a conventional separation apparatus setup.

SUMMARY OF THE INVENTION

In general, it is an object of the present invention to provide a method and an improved apparatus for enhanced plasmapheresis. It is another object of the present invention to provide an improved separating apparatus for blood fractionation, for cell washing of blood autotransfusion, for bone marrow transfusion, for peripheral stem cell transfusion, for extracorporeal pathogen reduction system, and the like. It is a further object of the present invention to provide a filtration system and methods thereof comprising a fluid supply containing filtrate and particulate constituent. The "particulate constituent" in a broad sense is herein meant to indicate the remaining substance other than the filtrate from the fluid supply.

Enhanced continuous plasmapheresis is accomplished by continually feeding a blood supply through a filtration chamber to effect separation of plasma components and cellular components. The blood passes in essentially parallel manner to the plane of the filtration membrane at flow rates sufficient to create shear stress across the membrane in the order of 10 to 2,000 dynes/cm$^2$, a preferred range being from about 100 to about 1,000 dynes/cm$^2$. In one aspect, the membrane has a pore size, pore shape, and cells affinity adequately sufficient to allow the plasma components to pass therethrough but retain cellular components thereon. Generally pore sizes of from 0.2 to 1.0 microns are preferred for plasma or platelet separation. Transmembrane pressure of from about 10 mmHg to about 1,000 mmHg is employed to separate the blood supply into cellular components and plasma fractions. With assistance of the orbital motion of the membrane, the local flow rate and shear stress can be controlled, resulting in a narrower range of the transmembrane pressure that has lower hemolysis and lower plugging propensity.

In order to accomplish the enhanced plasmapheresis, a filtration system may comprise a filtration chamber having a hollow interior enclosed by a first plate, a second plate, and a flexible circumferential seal element between the first plate and the second plate, wherein the first plate is either essentially parallel to or at an acute angle to the second plate so as to form a chamber gap for the hollow interior. The filtration system further comprises a fluid supply means for supplying a fluid containing filtrate and particulate constituent; means for directing the fluid supply into the hollow interior; and a filtrate collecting means for directing the filtrate passing through the filter membrane means to a collecting means and a particulate constituent collecting means for directing from the chamber gap a remaining constituent of the fluid supply out of the chamber. The second plate comprises filter membrane means for separating filtrate from the particulate constituent, and wherein the second plate is detachably coupled to a non-rotational drive structure that controls the second plate in an orbital motion in reference to a center axis of the first plate.

The term "orbital motion", when used herein, refers to a motion that moves back and force between two points in a continuous manner, wherein the route of the backward movement may either partially overlap or not overlap the route of the forward movement. However, the "orbital motion" is different from "rotation" as referred and defined in this patent application. "Rotation" is defined as a movement in such a way that all particles follow circles with a common angular velocity about a common axis. (Webster's New Collegiate Dictionary, G & C Merriam Co. 1980)

In a preferred embodiment, a blood filtration apparatus may comprise a chamber having a hollow interior enclosed by a first plate, a second plate, and a flexible circumferential seal element between the first plate and the second plate, wherein the first plate is either essentially parallel to or at an acute angle to the second plate so as to form a chamber gap for the hollow interior; wherein the second plate comprising filter membrane means for separating plasma constituent from the blood, wherein the second plate is detachably coupled to a non-rotational drive structure that controls the second plate in an orbital motion in reference to a center axis of the first plate. The blood filtration apparatus system further comprises means for directing a blood supply into the chamber gap; means for directing the plasma constituent passing through the filter membrane means to a collecting means; and means for directing from the chamber gap a remaining constituent of the blood out of the chamber. In another aspect, the filter membrane means comprises two or more filter membranes spaced apart and with different separation characteristics for separating a supply of multiple constituents. One example of the supply of multiple constituents is blood that includes red blood cells, white cells, platelet, plasma and other minor components.

In a still further embodiment, a blood filtration method for use in separating filtrate from blood supply comprises the steps of (a) feeding the blood supply into a chamber having a hollow interior enclosed by a first plate, a second plate, and a flexible circumferential seal element between the first plate and the second plate, wherein the first plate is either essentially parallel to the second plate or at an acute angle to the second plate so as to form a chamber gap for the hollow interior; the second plate comprising filter membrane means for separating filtrate constituent from the blood, wherein the second plate is detachably coupled to a non-rotational drive structure that controls the second plate in an orbital motion in reference to a center axis of the first plate; (b) initiating orbital motion of the second plate by the non-rotational drive structure to effect enhanced separation of filtrate from blood supply; (c) collecting the filtrate constituent passing through the filter membrane means; and (d) discharging a remaining constituent of the blood from the chamber gap out of the chamber. The blood supply may comprise at least one component selected from the group consisting of red blood cell, white blood cell, and platelet.

In one aspect, a method of treating virus-infected blood including, but not limited to, HIV infections and AIDS caused by enveloped viruses having a lipid envelope and spikes covered by glycoproteins comprising separating the blood supply into substantially uninfected components and substantially infected components including plasma and white cells using at least one separation chamber having appropriate separating membrane with orbital motion. The method further comprises de-virusing the lipid-associated virus with a de-virusing agent, followed by recovering the non-virulent plasma for reinfusion purposes. The term "de-virusing" is intended herein to mean eliminating or decontaminating the virulent effects of virus. The de-virusing is intended to render the virus-infected substance less virulent, not necessarily eliminating the non-virulent virus body.

Some aspects of the invention relate to an extracorporeal pathogen reduction system comprising means for withdrawing blood from a patient, means for separating a plasma constituent from the blood, means for inactivating pathogen in the plasma constituent, and means for returning treated plasma constituent to the patient. In one embodiment, the means for separating a plasma constituent from the blood comprises a blood filtration apparatus characterized by an orbital motion with filter membrane means. In another embodiment, the means for inactivating the pathogen comprises adding at least one photosensitizer into the plasma constituent and providing photosensitized inactivation to the pathogen at an effective amount of radiation.

Some aspects of the invention relate to a method of extracorporeally reducing pathogen burden of a patient comprising: filtering the patient's blood through a blood filtration apparatus configured for separating a plasma constituent from the blood; passing the plasma constituent through pathogen-reduction means for reducing the pathogen burden in the plasma constituent; and returning cellular components of the patient's blood back to the patient. In one embodiment, the filtering step is carried out with the blood filtration apparatus comprising a chamber having a hollow interior enclosed by a first plate, a second plate, and a flexible seal element between the first plate and the second plate, wherein the first plate is either essentially parallel to or at an acute angle to the second plate so as to form a chamber gap for the hollow interior; means for directing blood into the chamber gap; a non-rotational drive structure; the second plate comprising the filter membrane means for separating plasma constituent from the blood, wherein the second plate is detachably coupled to the non-rotational drive structure that controls the second plate in an orbital motion in reference to a center axis of the first plate; a collecting means; means for directing the plasma constituent passing through the filter membrane means to the collecting means; and means for directing from the chamber gap a remaining constituent of the blood out of the chamber.

It is therefore some aspect of the present invention to provide an apparatus system and methods thereof for biological separation and therapies, such as platelet collection, viral particle de-virusing/removal, cell washing and processing for stem cell selection, bone marrow purging, red blood cell collection, auto-transfusion, auto-immune disease treatment, selective macro-molecule removal, toxin removal, LDL removal, extracorporeal plasma delipidation, extracorporeal pathogen reduction system, HIV treatment, and the like.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 9, what is shown is an embodiment of the enhanced separation process employing a separation chamber system comprising a filter membrane chamber and/or a treatment chamber under an orbital motion arrangement. The enhanced separation process is particularly applicable for plasmapheresis and other medical applications, such as for blood fractionation, for blood autotransfusion, for bone marrow transfusion, for peripheral stem cell transfusion, for HIV removal, for general delipidation, for plasma de-virusing, for pathogen inactivation, and the like.

Figure 1:
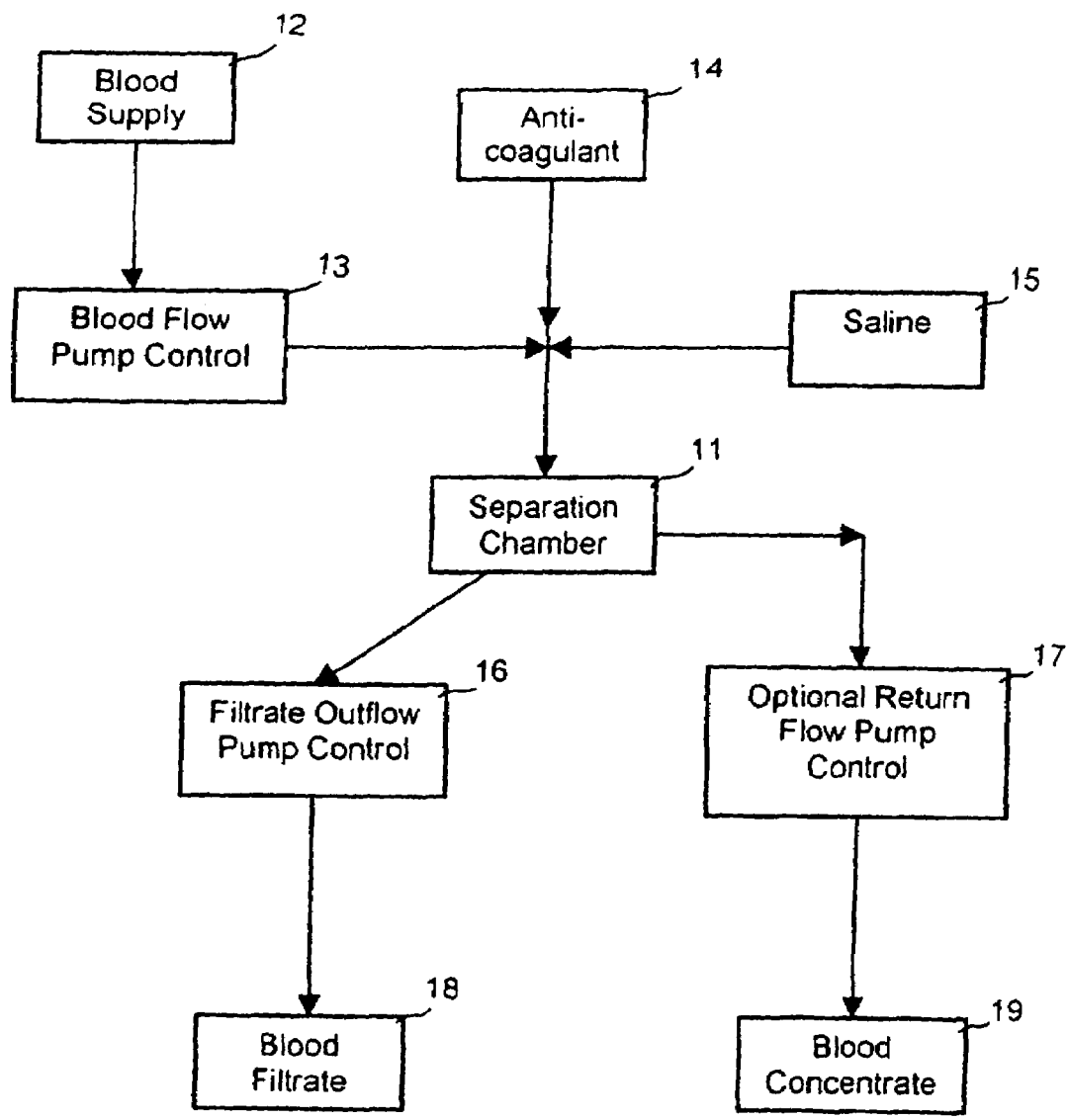
FIG. 1 is a schematic diagram of an enhanced blood separation process employing a separation chamber comprising a filter membrane under an orbital motion of the present invention.

FIG. 1 shows a schematic diagram of an enhanced blood separation process employing a separation chamber comprising a filter membrane under an orbital motion of the present invention. The blood supply 12 to the apparatus 11 may comprise fresh whole blood, thawed blood, or partially fractionated blood such as white blood cells containing plasma. The blood supply is fed to the separation chamber 11 via a blood flow pump control 13 or other means for directing a blood into the separation chamber 11. To prevent the blood supply from coagulation, anticoagulant 14 may optionally be added into the blood supply at an appropriate point of the blood supply feeding line. Similarly, saline or intravenous fluids 15 may optionally be added during the blood-feeding step or returning step. A positive pressure is generally maintained during the plasmapheresis of the present invention. The pressure difference across the membrane is preferably in the range of 10 to 1000 mm of mercury. The pressure difference is controlled by the flow rates of the blood flow pump control 13, the filtrate outflow pump control 16 and/or the return flow pump control 17.

Blood filtrate 18 is collected from the opposite side of the filter membrane, wherein the filtrate collecting means is completely isolated from communication with the blood supply. The filtrate is collected from the separation chamber 11 via a filtrate outflow pump control 16 or other means for directing the plasma constituent passing through the filter membrane. Blood concentrate 19 or the cellular constituent portion is withdrawn from the separation chamber 11 via an optional return flow pump control 17 or other means for directing a remaining constituent of the blood out of the chamber.

The pressure drops across the filter membrane can be adjusted by manually adjusting one or more of the flow pump controls 13, 16, and 17, or by providing automatic adjusting mechanisms. The pressure drop may be measured by an optional differential pressure indicator and/or controlled by the automated adjusting mechanisms.

Figure 2:
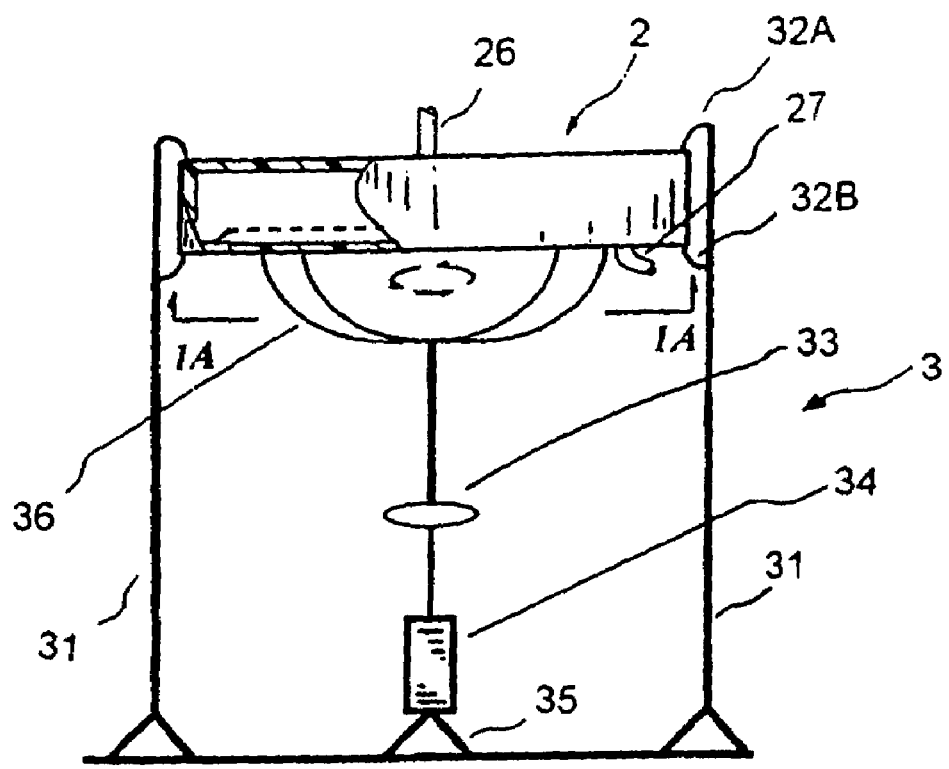
FIG. 2 is an illustrative setup of an enhanced blood separation process employing a separation chamber comprising a filter membrane under an orbital motion.

FIG. 2 shows an illustrative setup of an enhanced blood separation process employing a separation chamber comprising a filter membrane under an orbital motion. A plasmapheresis setup comprises a supporting installation 3 that can be rolled away or placed at any convenient location and a detachably removable blood filtration apparatus 2. The supporting installation 3 comprises a plurality of supporting poles 31 and a rotatable means 34 for generating orbital motion through a non-rotational structure 33 to the blood filtration apparatus 2. The rotatable means 34 may be selected from the group consisting of a rotatable magnetic motor, a rotatable mechanical motor and the like, wherein the rotatable means 34 is firmly attached to the supporting installation 3 via an attachment 35.

Each supporting pole 31 has a couple of grabbing pins 32A, 32B for securely and firmly holding the blood filtration apparatus 2 in place when the removable blood filtration apparatus 2 is placed into the supporting installation 3. The grabbing pins 32A, 32B are generally equipped with a spring-like mechanism for releasing the blood filtration apparatus 2 when the apparatus needs to be removed from the supporting installation 3. The supporting poles 31 are so designed that the blood filtration apparatus 2 when placed into slots of the grabbing pins 32A, 32B is always at a level without undue vibration caused by the rotatable means 34.

The separation chamber 4 that is reasonably sealed from leaking may be installed horizontally, vertically or at any angle. However, for space-saving purposes and taking into consideration of gravity, a preferred setup is a horizontal separation chamber detachably coupled to a vertical non-rotational structure 33.

In an illustrative example, a mechanical motor is used as the rotatable means 34. One end of an elongate shaft is secured to an axis of the mechanical motor while the end of the elongate shaft has a cam. The non-rotational drive structure 33 intimately contacts an edge of the cam and is indirectly coupled to the rotatable means 34 for generating orbital motion to the second plate. Therefore, when the cam rotates, the non-rotational drive structure 33 moves in an orbital motion. The frequency of the orbital motion is related to the rotational frequency of the motor while the off-center distance of the orbital motion is related to the diameter and shape of the cam.

Figure 3:
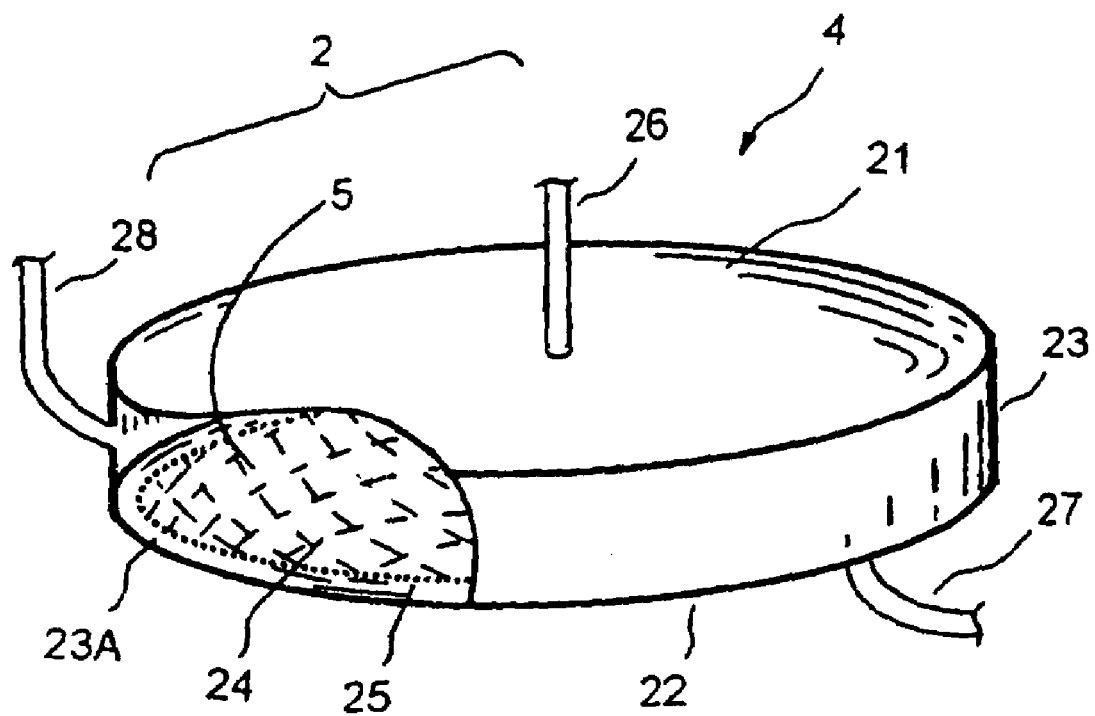
FIG. 3 is a perspective view of the blood filtration apparatus comprising the separation chamber having a filter membrane.

FIG. 3 shows a perspective view of the blood filtration apparatus 2 comprising a separation chamber 4 having a filter membrane 24. The blood filtration apparatus 2 comprises a separation chamber 4, means 26 for directing a blood into the chamber gap, means 27 for directing the plasma constituent that just passes through the filter membrane means to a collecting means, and means 28 for directing from the chamber gap a remaining constituent of the blood out of the separation chamber 4.

The separation chamber 4 comprises a hollow interior 5 enclosed by a first plate 21, a second plate 22, and a flexible circumferential seal element 23 between the first plate 21 and the second plate 22, wherein the first plate 21 is either essentially parallel to or at an acute angle to the second plate 22 so as to form a chamber gap for the hollow interior 5. The second plate 22 comprises filter membrane means 24 for separating plasma constituent from the blood, wherein the second plate 22 is detachably coupled to a non-rotational drive structure 33 that controls the second plate 22 in an orbital motion in reference to a center axis of the first plate 21. The chamber 4 is generally detachable from the non-rotational drive structure 33.

The location of the means 26 for directing a blood into the chamber gap may be selected from the group consisting of at about a center of the first plate, at about periphery of the first plate, and at about a corner of the first plate. Similarly, the location of the means 27 for directing the plasma constituent to a collecting means may be selected from the group consisting of at about periphery of the second plate, at about a center of the second plate, and at about a corner of the second plate. The above-mentioned location is determined by the application, the design and the construction of the blood filtration apparatus. In a preferred setup for a horizontal separation chamber 4, the means 26 for directing a blood supply 12 into the chamber gap may be from the top of the separation chamber downward toward the filter membrane 24 or from the bottom of the separation chamber upward toward the filter membrane. To maintain the cellular components in a suspension mode by gravity, the means for blood supply upward toward the separation membrane may be preferred.

In one preferred embodiment, the acute angle between the first plate and the second plate is in the range of 1 degree to 40 degrees so that the concentration polarization effect is minimized. The acute angle may preferably be in the range of 1 degree to 15 degrees. The acute angle may be measured from one side of the two plates to another side of the plates, from the center to the periphery of the plates or in other arbitrary manner.

The flexible circumferential seal element 23, 23A may be selected from the group consisting of silicone, polyurethane, latex, Nylon, polyvinyl chloride, polyimide, polycarbonate, polyacrylate, polymethacrylate, polystyrene, polyethylene, polypropylene, their mixture, and their copolymer. The flexible circumferential seal element of the present invention refers to a seal material that is flexible and fluid-tight so that the second plate 22 can move in an orbital motion in reference to a center axis of the first plate 21.

The filter membrane means 24 (such as the one for separating the plasma constituent from the human blood) may be selected from the group consisting of nylon membrane, polycarbonate membrane, polysulfone membrane, polyimide membrane, oval pore membrane, micro-fabricated membrane, tract-edged membrane, a combination of the above and the like. In a preferred embodiment, the filter membrane means 24 is partially attached to the second plate 22 at periphery 25 of the second plate 22 so that a space below the filter membrane 24 has no fluid communication with the chamber interior 5 except through the membrane 24 itself. The periphery 25 of the second plate 22 is joined with the flexible circumferential seal element 23 by a flexible seal material 23A so that the two plates 21, 22 can move orbitally, but not rotate, relative to each other.

In order to maximize the separation efficiency, the separation chamber can be in a round shape or in other appropriate shape to take advantages of the orbital motion or movement of the second plate. The filter membrane can also be in a round shape or in other appropriate shape. The filter membrane and its properties for separating blood supply or other solute-containing fluid are well known to one of ordinary skill in the art.

The main purpose of a filter membrane 24 of the present invention is to separate one component in a fluid from other constituents. It is one aspect of the present invention to coat or securely load a substrate onto a filter membrane to enhance separation or apheresis. One example is to coat heparin onto a membrane enabling reducing any clot or platelet adhesion onto the membrane. In another aspect of the present invention, the substrate is an antibody enabling selectively coupling with the corresponding antigen in the solution for effective antigen removal.

The interior surface of the second plate 22 facing the downstream side of the filter membrane 24 may be ribbed and/or studded. It is adapted for allowing the plasma constituent to pass through the filter membrane means onto the spaces between the ribs and/or studs of the interior surface and subsequently to the collecting means 27. The pattern of ribs may be selected from the group consisting of concentric circular ribs, hexagonal ribs, square ribs and the like. The studs can be in any fashion on the interior surface of the second plate. In an alternate embodiment, the middle portion of the filter membrane 24 is detached from the interior surface of the second plate 22. A vibration means for causing the middle portion of the membrane to vibrate so as to minimize membrane clogging during blood filtration may be optionally provided. The vibration means may comprise an electromagnetic mechanism.

To effect the optimal plasma filtration, the filter membrane usually has pores of a size about 0.1 to 30 $\mu$m, preferably about 0.2 to 1.0 $\mu$m. A more preferred range of pore size is around 0.4 to 0.6 $\mu$m. The selection of pore size may vary with the goal of a particular separation process. As exemplary of membranes having the preferred properties for plasmapheresis with an orbital movement are HT 450 polysulfone membrane commercially available from Gelman Sciences, Inc., the polyester and polycarbonate membranes commercially available from Nuclepore Corporation.

The chamber gap may be between 0.001 and 0.1 inch for generating optimal local flow rate and local shear force for plasma filtration process. A preferred range of chamber gap is about 0.03 to 0.06 inch. The optimal shear force for enhanced filtration process of the present invention is a function of a combination of the chamber gap, the flow rates of the fluid supply and the outflow filtrate, and the orbital motion characteristics, wherein the orbital motion characteristics may comprise the orbiting frequency, orbiting distance, and orbiting manners. A preferred range of shear force is around 100 to 1,000 dynes/cm$^2$.

Figure 8:
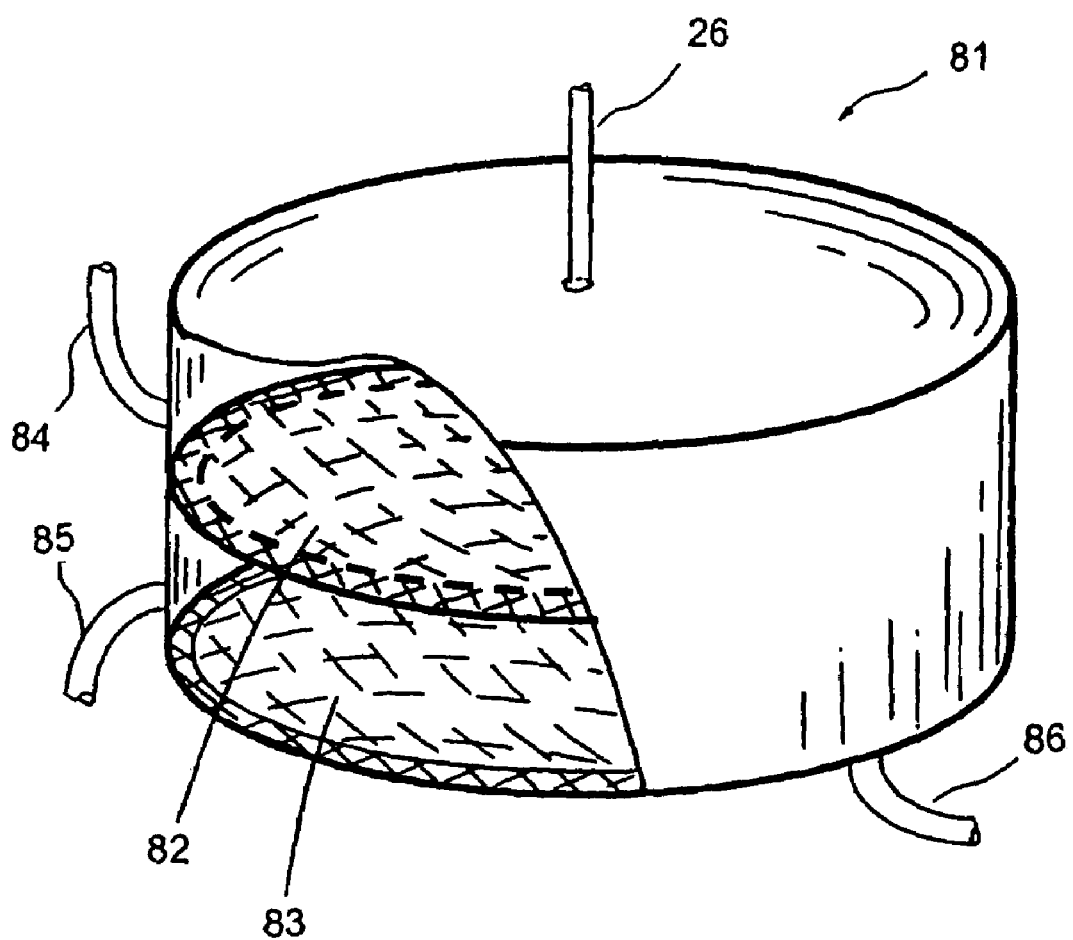
FIG. 8 is a perspective view of the blood filtration apparatus comprising the separation chamber having two filter membranes.

In another aspect, the filter membrane means comprises a plurality of filter membranes 82, 83 spaced apart and with different separation characteristics for separating a supply of multiple constituents. One example of the supply of multiple constituents is blood that includes red blood cells, white cells, platelet, plasma and other minor components. FIG. 8 shows a perspective view of the blood filtration apparatus 2 comprising a separation chamber 81 having two filter membranes 82, 83, wherein the blood filtration apparatus further comprises means 26 for directing a blood supply into the chamber gap, means 85 for directing the white cells constituent that passes through the first filter membrane 82 for disposal or treatment, means 86 for directing the plasma constituent that passes through the second filter membrane 83 to collecting means, and means 84 for directing from the chamber gap a remaining constituent, primary red blood cells of the blood supply out of the separation chamber 81.

Figure 4:
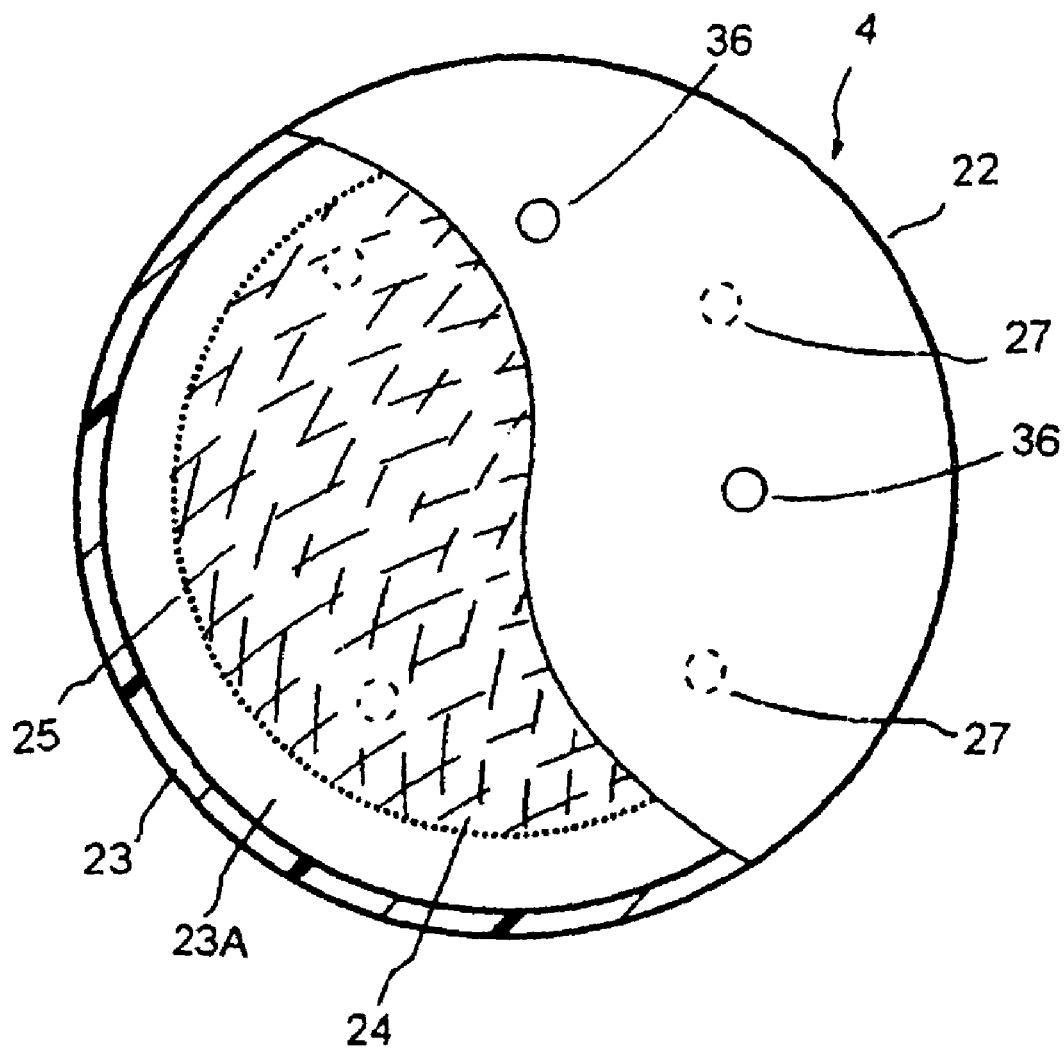
FIG. 4 is a bottom view of the separation chamber for section 1A—1A of FIG. 2

FIG. 4 shows a bottom view of the separation chamber 4 from section 1A—1A of FIG. 2 or 81 in FIG. 8. A plurality of coupling elements 36 is part of the non-rotational drive structure 33, wherein the coupling element 36 is detachably coupled to an exterior side of the second plate 22 of the separation chamber 4 for causing the second plate 22 to have an orbital motion in reference to a center axis of the first plate 21. The orbital motion or movement may be selected from the group consisting of clockwise movement, counterclockwise movement and a combination of the above. The off-center orbital motion or movement is generally within a range of 0.001 to 1.0 inch distance. More preferably, the off-center orbital motion is in the range of about 0.05 to 0.5 inch distance. In a further embodiment, the orbital motion may be at a frequency within a range of 100 to 50,000 cycles per minute. The frequency of the orbital motion is preferred in the range of 1,000 to 20,000 cycles per minute. The pattern of the orbital motion or movement may be selected from the group consisting of circular shape movement, oval shape movement, peanut shape movement, pear shape movement, and irregular shape movement.

For application, a blood filtration method for use in separating filtrate from blood supply comprises the steps of (a) feeding blood supply into a separation chamber comprising filter membrane means for separating filtrate constituent from the blood; (b) initiating orbital motion of the filter membrane to effect enhanced separation of filtrate from blood supply; (c) collecting the filtrate constituent passing through the filter membrane; and (d) discharging a remaining constituent of the blood out of the separation chamber and/or returning to the donor.

Combined Separation Chamber System

Figure 5:
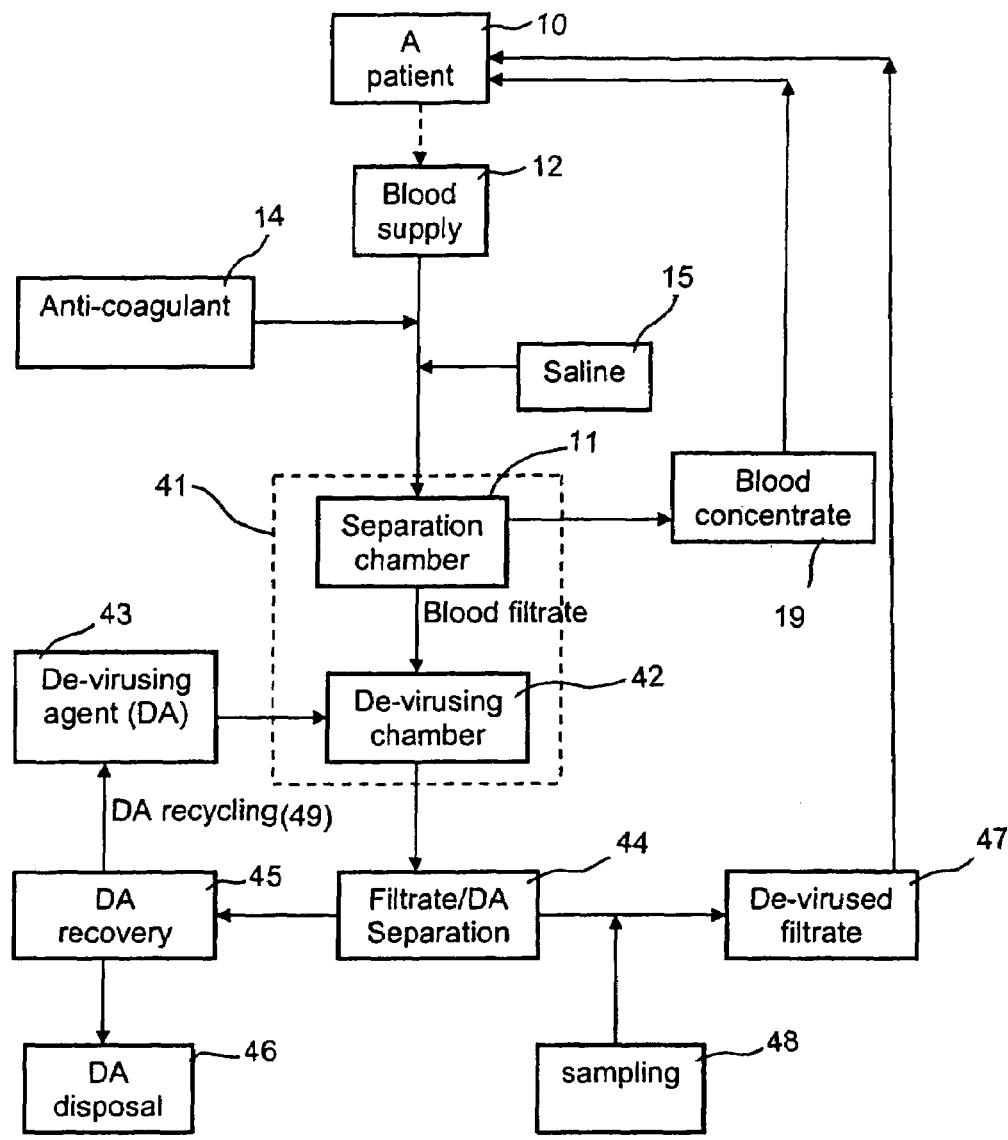
FIG. 5 is a further schematic diagram of the separation and treatment system for HIV-infected patients or other autoimmune patients.

To utilize the special orbital motion disclosed herein for blood components separation with subsequent de-virusing treatment, FIG. 5 shows a further schematic diagram of a combined separation and treatment system for treating virus-infected patients or other patients needing blood components reinfusion. The virus to be deactivated in the instant invention may include an HIV virus, an AIDS virus, a human papilloma virus, a hepatitis B virus, an immunodeficiency virus, a T lymphotrophic virus, a herpesvirus, a measles virus, an influenza virus, and the like. As shown and described in FIG. 1 in one aspect, the blood supply 12 from a patient 10 is introduced into the separation chamber 11. Typically, the withdrawal of blood is accomplished via a needle or catheter inserted in the right antecubital vein. The return of the treated blood is also accomplished by the use of a needle or catheter inserted into the left antecubital vein. The combined separation chamber system 41 (shown within the enclosure of the broken lines in FIG. 5) comprises a separation chamber 11 and a de-virusing chamber 42. The blood concentrate 19 from the separation chamber 11 of the system 41 is essentially virus free. In one illustrative aspect, the de-virusing chamber 42A and the separation chamber 11A are integral part of a combined system 51 of FIG. 6. In another illustrative aspect, the de-virusing chamber 42B and the separation chamber 11B constitute two parts of a combined system 61 of FIG. 7.

In one aspect, the blood filtrate 18 may comprise the infected plasma containing cell-free virus and/or the infected cells containing replicating virus. The blood filtrate is introduced into the de-virusing chamber 42 of FIG. 5, wherein a de-virusing agent (DA) 43 is also introduced into the de-virusing chamber 42 for mixing intimately with and de-virusing the infected plasma. In one preferred aspect, the de-virusing chamber 42 is under an orbital motion of the present invention that has optimal local shear forces and desired quality mixing/de-virusing. In one aspect, the de-virusing agent comprises hydrocarbons, ethers, alcohols, and mixtures thereof. In another aspect, the de-virusing agent comprises gamma-cyclodextrin, beta-cyclodextrin, alpha-cyclodextrin, its analog and derivatives. In still another aspect, the de-virusing agent comprises mixtures of hydrocarbons, ethers, alcohols, and beta-cyclodextrin, its analog and derivatives.

Hildreth in U.S. patent application Publication 2002/0128227 and Publication 2002/0132791, entire contents of which are incorporated herein by reference, discloses a method of reducing the risk of transmission of a sexually transmitted pathogen comprising contacting the pathogen or cells susceptible to infection by the pathogen with a beta-cyclodextrin, wherein the pathogen is an enveloped virus selected from a group consisting of an immunodeficiency virus, a T-lymphotrophic virus, a herpesvirus, a measles virus, and an influenza virus. The plasma de-virusing process by beta-cyclodextrin (and/or alpha-cyclodextrin, gamma-cyclodextrin) is carried out in the de-virusing chamber 42, wherein the beta-cyclodextrin disrupts the enveloped virus, blocks the ability of the pathogen to infect an otherwise susceptible cell.

De-Virusing Agent β-Cyclodextrin

Beta-cyclodextrins are widely used as solubilizing agents, stabilizers, and inert recipients in pharmaceutical compositions (see U.S. Pat. Nos. 6,194,430, 6,194,395, and 6,191,137, each of which is incorporated herein by reference). Beta-cyclodextrins are cyclic compounds containing seven units of alpha-(1,4) linked D-glucopyranose units, and act as complexing agents that can form inclusion complexes and have concomitant solubilizing properties (see U.S. Pat. No. 6,194,395; see, also, Szejtli, J. Cyclodextrin Technol. 1988). As disclosed herein, beta-cyclodextrins also can block passage of a sexually transmitted pathogen through the membrane of a susceptible cell by disrupting the enveloped lipid in cell membrane.

The compositions and methods of the invention are exemplified using 2-hydroxypropyl-beta cyclodextrins (2-OH-βCD). However, any beta-cyclodextrin derivative can be used in a composition or method of the invention, provided the beta-cyclodextrin derivative disrupts enveloped lipid (that is, a lipid raft) in the membranes of cells susceptible to a sexually transmitted pathogen without causing undesirable side effects. Beta-cyclodextrins act, in part, by removing cholesterol from cell membranes, and different beta-cyclodextrins are variably effective in such removal. For example, methyl beta-cyclodextrin removes cholesterol from cell membranes very efficiently and quickly and, as a result, can be toxic to cells, which require cholesterol for membrane integrity and viability. In comparison, a beta-cyclodextrin derivative such as 2-OH-βCD can effectively remove cholesterol from cells without producing undue toxicity. Thus, it will be recognized that a β-cyclodextrin (α-cyclodextrin, or γ-cyclodextrin) useful in a composition or method of the invention is one that removes cholesterol in an amount that disrupts enveloped lipid, without substantially reducing cell viability (see, for example, Rothblat and Phillips, J. Biol. Chem. 257:4775–4782, 1982, which is incorporated herein by reference).

Beta-cyclodextrins useful in the present invention include, for example, beta-cyclodextrin derivatives wherein one or more of the hydroxy groups is substituted by an alkyl, hydroxyalkyl, carboxyalkyl, alkylcarbonyl, carboxyalkoxyalkyl, alkylcarbonyloxyalkyl, alkoxycarbonylalkyl or hydroxy-(mono or polyalkoxy)alkyl group or the like; and wherein each alkyl or alkylene moiety contains up to about six carbons. Substituted beta-cyclodextrins that can be used in the present invention include, for example, polyethers (see, for example, U.S. Pat. No. 3,459,731, which is incorporated herein by reference); ethers, wherein the hydrogen of one or more beta-cyclodextrin hydroxy groups is replaced by C1 to C6 alkyl, hydroxy-C1–C6-alkyl, carboxy-C1–C6 alkyl, C1–C6 alkyloxycarbonyl-C1–C6 alkyl groups, or mixed ethers thereof. In such substituted beta-cyclodextrins, the hydrogen of one or more beta-cyclodextrin hydroxy group can be replaced by C1–C3 alkyl, hydroxy-C2–C4 alkyl, or carboxy-C1–C2 alkyl, for example, by methyl, ethyl, hydroxyethyl, hydroxypropyl, hydroxybutyl, carboxymethyl or carboxyethyl. It should be recognized that the term "C1–C6 alkyl" includes straight and branched saturated hydrocarbon radicals, having from 1 to 6 carbon atoms. Examples of beta-cyclodextrin ethers include dimethyl-beta-cyclodextrin Examples of beta-cyclodextrin polyethers include hydroxypropyl-p-beta-cyclodextrin and hydroxyethyl-beta-cyclodextrin (see, for example, Nogradi, "Drugs of the Future" 9(8):577–578, 1984; Chemical and Pharmaceutical Bulletin 28: 1552–1558, 1980; Yakugyo Jiho No. 6452 (Mar. 28, 1983); Angew. Chem. Int. Ed. Engl. 19: 344–362, 1980; U.S. Pat. No. 3,459,731; EP-A–0,149, 197; EP-A–0,197,571; U.S. Pat. No. 4,535,152; WO-90/12035; GB-2,189,245; Szejtli, "Cyclodextrin Technology" (Kluwer Academic Publ. 1988); Bender et al., "Cyclodextrin Chemistry" (Springer-Verlag, Berlin 1978); French, Adv. Carb. Chem. 12:189–260; Croft and Bartsch, Tetrahedron 39:1417–1474, 1983; Irie et al., Pharm. Res. 5:713–716, 1988; Pitha et al., Internat'l. J. Pharm. 29:73, 1986; U.S. Pat. No. 5,134,127 A; U.S. Pat. Nos. 4,659,696 and 4,383,992, each of which is incorporated herein by reference; see, also, U.S. Pat. No. 6,194,395).

Some aspects of the invention provides the pathogen-reduction means comprising cyclodextrin being added into the plasma constituent in an amount and for a period of time sufficient to inactivate the pathogen, wherein the cyclodextrin is selected from a group consisting of an α-cyclodextrin, a β-cyclodextrin, a γ-cyclodextrin and a derivative thereof. Further, some aspects of the invention relate to the pathogen-reduction means comprising cladribine being added into the plasma constituent in an amount and for a period of time sufficient to inactivate the pathogen.

After plasma de-virusing, the de-virusing agent is separated from the treated plasma (that is, de-virused filtrate 47) in an apparatus setup 44 of FIG. 5, wherein the de-virusing agent is recovered 45, disposed of 46 or recycled 49 after proper treatment of ridding the virus. The filtrate/DA separation step 44 may be carried out by vacuum distillation, liquid-liquid extraction, adsorptive separation, or other known techniques. The treatment of the contaminated DA for recycling purposes can be carried out by vacuum distillation, filtration, sterilization, or other known techniques. The de-virused filtrate 47 is properly and timely sampled and monitored by a setup 48, such as Gas Chromatography or other appropriate instrument to ensure the de-virused filtrate 47 meets the requirements for reinfusion or other medical purposes. The de-virused filtrate 47 may optionally be reinfused into the patient 10. Saline, nutrients, or intravenous fluids may be added to the returning streams, such as the streams of blood concentrate 19 or the de-virused filtrate 47.

Figure 6:
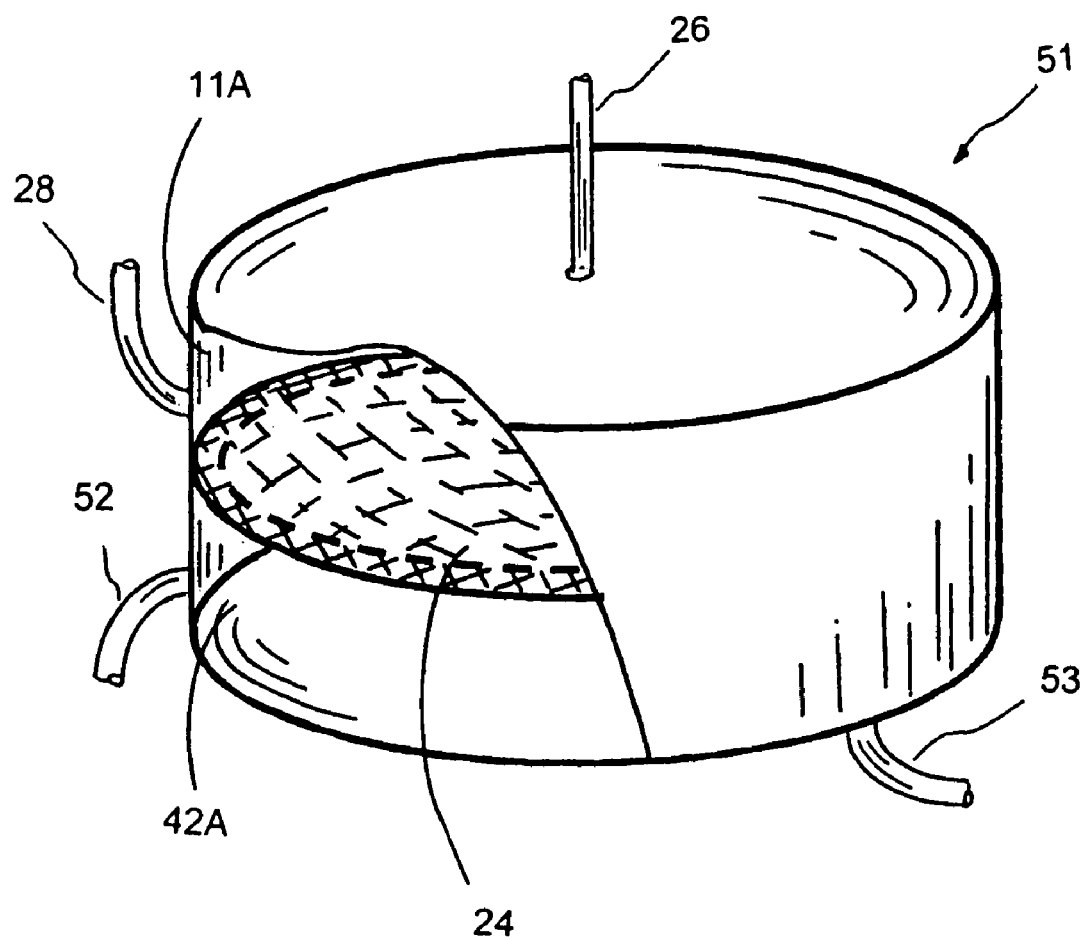
FIG. 6 is one embodiment of a combined separation chamber system for plasma de-virusing according to the principles of the present invention.

FIG. 6 shows one embodiment of a combined separation chamber system 51 for plasma de-virusing according to the principles of the present invention, wherein the system 51 comprises an upper chamber 11A and a lower chamber 42A separated by a filtering membrane 24. In another aspect, a system comprises a plurality of filtering membranes, such as the one in FIG. 8, is also applicable. The combined chamber system 51 may comprise means 26 for directing a blood into the chamber gap, means 52 for infusing the de-virusing agent (DA) 43 into the de-virusing chamber 42A, means 53 for directing the de-virused plasma constituent along with the de-virusing agent 43 into a filtrate/DA separation setup 44, and means 28 for directing from the chamber gap a remaining constituent of the blood (that is, blood concentrate 19) out of the separation chamber 11A for reinfusion or other purposes. In this system, the upper blood separation chamber 11A and the lower de-virusing chamber 42A are integral parts of a combined system 51. Both chambers have the same orbital motion provided by the generating orbital motion through a non-rotational structure 33 to the blood filtration apparatus 2 as clearly described in FIG. 2. The rotatable means 34 may be selected from the group consisting of a rotatable magnetic motor, a rotatable mechanical motor and the like.

In configuration and apparatus design, the above-illustrated location in FIG. 6 for the means 26, 28, 52 and 53 is determined by the application, the engineering consideration and the construction of the blood processing apparatus 51. In a preferred setup for a horizontal separation chamber 51, the means 26 for directing a blood supply 12 into the separation chamber 11A may be from the top of the separation chamber downward toward the filter membrane 24 or from the bottom of the separation chamber upward toward the filter membrane 24. To maintain the cellular components in a suspension mode by gravity, the means for blood supply upward toward the separation membrane 24 may be preferred.

Figure 7:
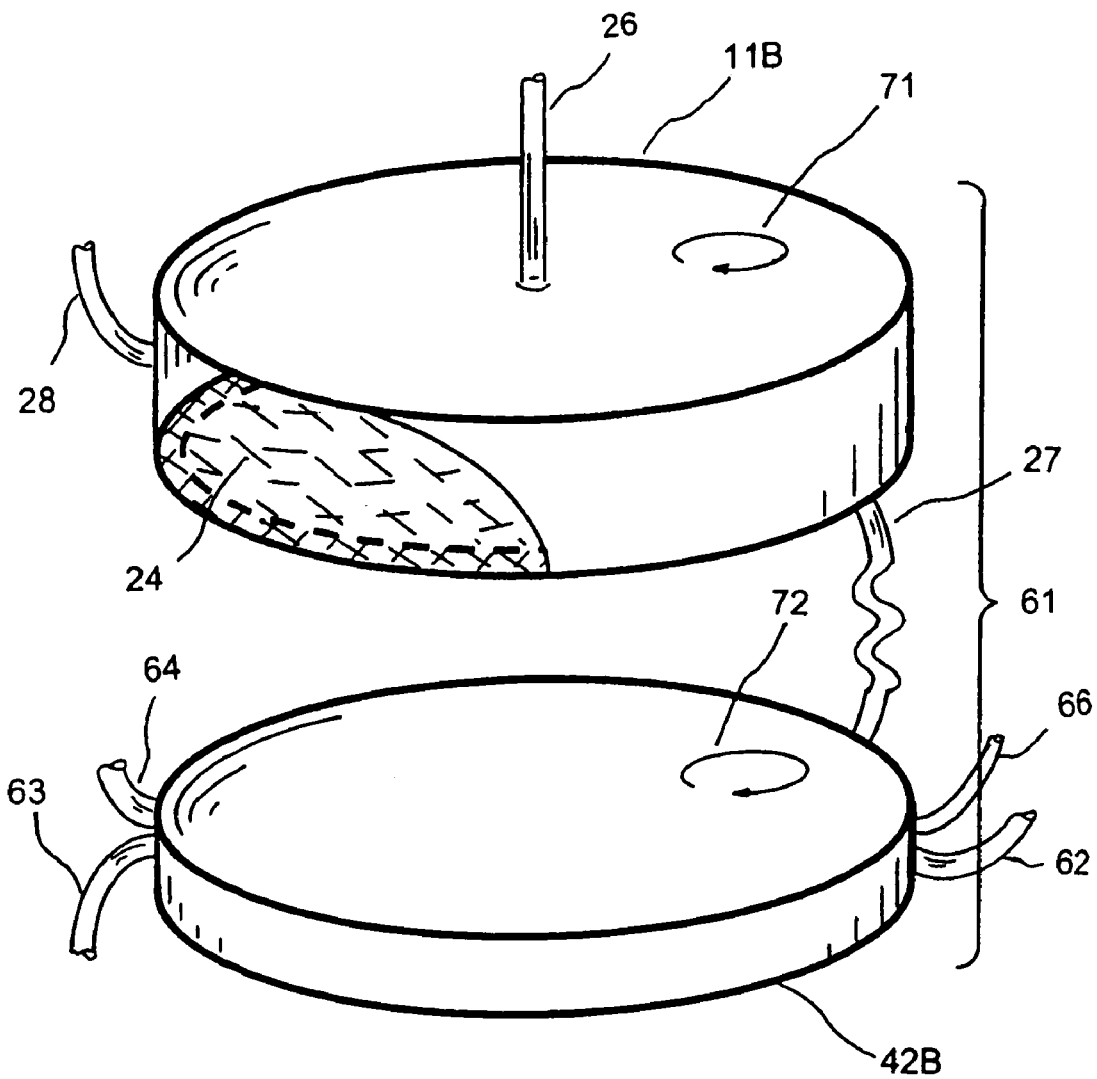
FIG. 7 is another embodiment of a combined separation chamber system for plasma de-virusing according to the principles of the present invention.

FIG. 7 shows another embodiment of a combined separation chamber system 61 for plasma de-virusing according to the principles of the present invention, wherein the system 61 comprising two chambers 11B, 42B connected by the means 27 which contains the virus-infected plasma constituent that just passes through the filter membrane means 24 of the separation chamber 11B. The means 27 serves as the input stream for the detached de-virusing chamber 42B. Each chamber 11B or 42B may be supported and energized separately by its own driver setup for the orbital motion indicated by an arrow 71, and 72, respectively. The orbital motion 71 for the separation chamber 11B and the orbital motion 72 for the de-virusing chamber 42B may be similar or different in direction, magnitude, speed, angle, or other characteristics.

As shown in FIG. 7, the combined system 61 comprises a separation chamber 11B similar to that shown in FIG. 3 and a de-virusing chamber 42B comprising means 62 for DA input, means 63 for directing the de-virused filtrate along with the contaminated DA to a filtrate/DA separation setup 44 (FIG. 5). In one aspect, when the de-virusing chamber 42B is further equipped with a proper vacuum separation means, an optional outlet means 64 for the vaporized DA is also provided. Gentle heat or cooling may be provided to the de-virusing chamber 42A, 42B for enhanced safe operations. Due to the volatility of some DA, the chamber 42A or 42B may be more efficient in de-virusing processes at a temperature below the room temperature, say, a few degrees lower than the room temperature. One example is to have at least 2 to 5° C. below the room temperature. In certain aspect, the de-virusing chamber 42B can be a conventional liquid-liquid extraction chamber or other suitable setup which is connected to an innovative separation chamber 11B of the present invention.

The conventional extracorporeal method and the liquid-liquid mixing process are well known to one who is skilled in the art, for example, a kidney dialysis method, a blood oxygenation method, a blood salvage process disclosed in U.S. Pat. No. 5,971,948, a delipidation process disclosed in U.S. Pat. No. 5,484,396, a solvent extraction process disclosed in U.S. Pat. No. RE37,584, or the like. They all suffer some disadvantages of low efficiency, low product quality, or being complicated in operations. According to the present invention, there is provided a method of treating virus-infected patient by de-virusing plasma and killing the enveloped virus in a combined chamber system having the orbital motion of the present invention. According to the present invention, the virus to be de-virused comprises an HIV virus, an AIDS virus, a human papilloma virus, a hepatitis B virus, an immunodeficiency virus, a T-lymphotrophic virus, a herpesvirus, a measles virus, an influenza virus, and combination thereof.

In some aspect, the combined separation chamber system 51, 61 for plasma de-virusing and HIV/AIDS treatment according to the principles of the present invention may comprise more than one separation chamber and/or more than one de-virusing chamber. It is sometimes advantageous to have, in combination, a first separation chamber for recovering the red blood cells, a second separation chamber for recovering platelets, and a third separation chamber for separating and disposing the virus-infected white cells, and a fourth separation chamber for separating and treating virus-containing plasma, and so forth. The separation efficiency is mostly affected by selecting the most proper filtering membrane sized and configured with appropriate orbital motion of the present invention. To enhance the mixing efficiency of the de-virusing chamber 42A, or 42B, the mixed filtrate/DA from the chamber 42A, 42B may be recirculated via the optional outlet means 64 or other outlet means back into the chamber at the inlet means 27 or at a spaced apart inlet port 66.

Naficy in U.S. Pat. No. 5,419,759 and U.S. Pat. No. 5,484,396, the entire contents of both being incorporated herein by reference, discloses that the HIV is an enveloped virus having lipids in its outer envelope. Some aspects of the invention provide an extracorporeal pathogen reduction system comprising: means for withdrawing blood from a patient; means for separating a plasma constituent from the blood; means for inactivating pathogen in the plasma constituent; and means for returning treated plasma constituent to the patient. The pathogen-reduction means for inactivating pathogen in the plasma constituent may comprise an organic solvent being added into the plasma constituent in an amount and for a period of time sufficient to inactivate the pathogen, wherein the organic solvent is selected from a group consisting of ethers, alcohols, volatile chlorinated hydrocarbons, acetone and chloroform that are well known to ones of ordinary skill in the art.

Therapeutic Plasmapheresis for Neurological Disorders

"Therapeutic plasmapheresis" is herein meant as a method for removing toxic or unwanted elements, for example, toxins, viral particle, LDL (low density lipoprotein), metabolic substances, and plasma constituents implicated in disease, such as complement or antibodies, from the blood of a patient. The therapeutic plasmapheresis (also referred as "therapeutic plasma exchange") is performed by removing blood, separating the plasma from the formed elements, and reinfusing the formed elements together with a plasma replacement back to the patient. It is one object of the present invention to provide a method for removing blood from a patient, separating the plasma from the formed elements, filtering the unwanted elements, such as toxins, viral particle, LDL, metabolic substances, and plasma constituents implicated in disease, such as complement or antibodies, and reinfusing the formed elements together with a plasma replacement back to the patient, wherein the filtering step utilizes a blood filtration apparatus characterized by an orbital motion of the present invention.

In one aspect, the ability to remove antibody and other immunologically active elements from the blood has led to the use of therapeutic plasmapheresis as a therapy for neurological conditions in which autoimmunity is believed to play a role. In some aspect of the present invention, the antibody and other immunologically active elements are removed from the blood by loading an antibody-specific antigen or an agent (or agents) that is specific to the immunologically active elements onto the filtering membrane of the present invention. It is estimated that one-half of the 20,000 to 30,000 TPE (therapeutic plasma exchange) procedures performed annually at present in the United States are done on patients with neurological disorders.

Many diseases, including myasthenia gravis, Lambert-Eaton syndrome, Guillain-Barré syndrome and others, are caused by a so-called autoimmune process. In autoimmune conditions, the body's immune system mistakenly turns against itself, attacking its own tissues. Some of the specialized cells involved in this process can attack tissues directly, while others can produce substances known as antibodies that circulate in the blood and carry out the attack. Antibodies produced against the body's own tissues are known as autoantibodies.

Pages et al. in U.S. Pat. No. 5,971,948, entire contents of which are incorporated herein by reference, discloses a vacuum-driven centrifuge-equipped apparatus for collection, washing and reinfusion of shed blood. The Pages et al. apparatus is distinguishable with a modified centrifuge bowl having a sealed aperture in its floor that permits reinfusion directly from the bowl without an additional reinfusion bag or reverse pump.

It is one object of the present invention to provide a method of treating autoimmune conditions of a patient comprising filtering the patient's blood through a blood filtration apparatus characterized by an orbital motion of the filter membrane means for separating a plasma constituent from the blood of the present invention and returning the cellular components back to the patient. In a further object of the present invention, the method comprises removing autoantibody from the patient's blood.

Delipidation With Enhanced Apheresis

The present invention discloses an apheresis apparatus having an orbital motion for the separation chamber with a proper membrane. In some aspect, the method may comprise processing plasma and removing the LDL (low density lipoprotein) from plasma without touching or damaging blood cells or activating platelet. LDL apheresis may generally include immunadsorption, dextran sulfate adsorption, heparin-induced extracorporeal LDL precipitation, and direct adsorption of lipoproteins, wherein an apheresis apparatus having a membrane-based separation chamber with an orbital motion of the present invention could be used for effective LDL apheresis.

In one embodiment for immunadsorption apheresis, an LDL-specific or LDL-reactive immune factor is loaded onto the filtering membrane of the separation chamber of the present invention, wherein LDL is effectively adsorbed by the LDL-specific or LDL-reactive immune factor upon passing the filtering membrane. In another embodiment for dextran sulfate adsorption, an LDL-specific or LDL-receptive dextran sulfate is loaded onto the filtering membrane of the separation chamber of the present invention, wherein LDL is effectively adsorbed by the LDL-specific or LDL-receptive dextran sulfate upon passing the filtering membrane.

In still another embodiment for heparin-induced extracorporeal LDL precipitation, an LDL-specific or LDL-receptive heparin is loaded onto the filtering membrane of the separation chamber of the present invention, wherein LDL is effectively adsorbed by the LDL-specific or LDL-receptive heparin upon passing the filtering membrane. The heparin-induced extracorporeal LDL precipitation apheresis may further comprise fibrinogen removal.

Jaeger and associates (Proceedings of 73rd European Atherosclerosis Society Congress #150, Salzburg, Austria 2002) report H.E.L.P. (heparin-mediated extracorporeal LDL/fibrinogen precipitation) apheresis for the treatment of acute myocardial infarction suffering from diffuse transplant coronary artery disease, incorporated herein by reference in its entirety.

Otto and associates (Proceedings of 73rd European Atherosclerosis Society Congress #185, Salzburg, Austria 2002) report long-term reduction of C-reactive protein by LDL apheresis leading to reduced risk for cardiovascular events, incorporated herein by reference in its entirety.

Konovalov and associates (Proceedings of 73rd European Atherosclerosis Society Congress #259, Salzburg, Austria 2002) report LDL apheresis leading to stabilization and even regression of atherosclerotic plaques in coronary arteries, incorporated herein by reference in its entirety.

Moriarty and associates (Proceedings of 73rd European Atherosclerosis Society Congress #511, Salzburg, Austria 2002) report H.E.L.P. (heparin-mediated extracorporeal LDL/fibrinogen precipitation) apheresis for lowering cholesterol with reduction of inflammatory markers and rheological improvement as an early intervention in acute coronary syndromes, incorporated herein by reference in its entirety.

Kostner and associates (Proceedings of 73rd European Atherosclerosis Society Congress #754, Salzburg, Austria 2002) report an extracorporeal solvent extraction procedure that removes essentially all cholesterol and triglyceride from treated plasma while not affecting blood constituents, incorporated herein by reference in its entirety.

It is one aspect of the present invention to provide a method of plasma purification, including delipidation and removal of unwanted elements (for example, toxins, viral particle, metabolic substances, pathogens, and plasma constituents implicated in disease, such as complement or antibodies), for a patient comprising treating the patient's plasma through a plasma filtration apparatus having an orbital motion and returning the treated plasma back to the patient.

HIV Virus and CD4 Monitoring

Doctors use a test that 'counts' the number of CD4 cells in a cubic millimeter of blood. A normal count in a healthy, HIV-negative adult can vary but is usually between 600 and 1200 CD4 cells/mm$^3$.

In some cases, in order to help understand changes in the absolute CD4 count, the doctor may also assess what proportion of all lymphocytes are CD4 cells. This is called the CD4 percentage. In HIV-negative people, a normal result is around 40%. A CD4 percentage which falls below about 15% is thought to reflect a risk of serious infections.

Most people with HIV find that their CD4 count falls over time. This often happens at a variable rate, so the count can still be quite stable for long periods. It is useful to have the CD4 count measured regularly for two reasons: first, to monitor the immune system and second, to help monitor the effectiveness of any anti-HIV therapy a patient is undertaking.

If the CD4 count is persistently below 350, the immune system is slightly weakened and the patient is at a gradually increasing risk of infections the further it falls. If it drops below 200–250, the patient is at increased risk from serious infections. At this point, the doctor should offer drugs or therapy to try to prevent such infections. If the CD4 count starts to drop rapidly or falls below 350, particularly if the viral load is high, one may wish to consider starting anti-HIV treatments. If the CD4 count falls below 250–200, the patient is recommended to start treatments with anti-HIV drugs or de-virusing therapy of the present invention.

One effect of anti-HIV drugs or therapy may be to improve the state of the immune system that is crudely reflected in an increase in the CD4 count. Evidence suggests that the cells' ability to fight infections is also improved. Monitoring the changes in the CD4 count while one is taking anti-HIV therapy can help a patient to decide whether the treatment is effective. Factors other than HIV can affect your CD4 count including infections, time of day, smoking, stress and which lab tests the blood sample. Therefore, it is very important to watch the trend in the CD4 count over time, rather than to place too much emphasis on a single test which may be misleading. It is one aspect of the present invention to provide a method of monitoring the effectiveness of the de-virusing process by CD4 count. It is another aspect of the present invention to provide a method of continuing a de-virusing process until the increase in CD4 count (from the pre-de-virusing stage) is significant. The increase in CD4 count is preferably at least 10, more preferably at least 50 to be significant.

Applications for Enhanced Apheresis

In one aspect of the present invention, the enhanced apheresis enables quality platelet collection, wherein platelet can be collected directly from whole blood using the blood filtration apparatus having an orbital motion of the present invention with a proper membrane. It is another embodiment of the present invention to facilitate platelet collection by filtering the cell-less plasma after cells have been removed from the whole blood supply in a prior separation process.

In another aspect of the present invention, the enhanced apheresis enables quality viral particle removal with a proper membrane effective to allow sufficient amount of virus-free filtrate to pass through, wherein the viral particle can be removed because of its size, shape, affinity to the membrane, or anti-virus coating on the membrane.

In some aspect of the present invention, the enhanced apheresis enables quality cell washing and processing for stem cell selection and/or the bone marrow purging, wherein stem cells can be collected from the bone marrow or other sources using the filtration apparatus characterized by an orbital motion for the filtering membrane of the present invention with a proper membrane and at least one filtration step effective to allow sufficient amount of stem cells to be collected. In one embodiment, each filtration step may comprise a proper membrane for each specific filtering need. It is one object of the present invention to provide a method of cell washing for a patient comprising introducing a fluid supply into a filtration apparatus with a proper filtering membrane characterized by an orbital motion, wherein the fluid supply comprises cellular components and filtrate; treating the fluid supply through the filtration apparatus; separating cellular components from filtrate; and collecting purified filtrate. It is another object of the present invention to provide a second fluid supply comprising the separated cellular components with proper filtrate are introduced into a second filtration apparatus with a second filtering membrane characterized by an orbital motion for enhanced cell washing.

In still another aspect of the present invention, the enhanced apheresis enables quality red blood cell collection using the filtration apparatus having an orbital motion of the present invention with a proper membrane configured and sized for separating red blood cells from the whole blood with one step or multiple step filtration. The enhanced apheresis of the present invention is also applicable to auto-transfusion during surgery by returning red blood cells, white blood cells and platelets to the patient. The multiple step filtration is generally carried out by re-circulating a partially treated filtrate to a filtration apparatus.

In one further aspect of the present invention, the membrane surface may be modified, for example, treated with heparin enabling passing platelet or fibrinogen without clogging the membrane pores. In one embodiment, the membrane surface may be coated with an antibody for selectively removing the counterpart antigen in the fluid supply. In another embodiment, the membrane surface may be coated with an antigen for selectively removing the counterpart antibody in the fluid supply, for example used in autoimmune therapy. Multiple sclerosis (MS) is one example of the autoimmune diseases. In still another embodiment, the membrane surface may be treated by changing the charge characteristics on the membrane or add functional groups such as a hydroxyl group suitable for enhancing selective filtering a specific molecule or particulate constituent from the fluid supply.

Extracorporeal Pathogen Reduction System (EPRS)

An extracorporeal pathogen reduction (or inactivation) system (EPRS) is herein intended to mean a system to inactivate at least a portion of pathogens in an extracorporeal body fluid system. The extracorporeal method is readily known to those of skill in the art, for example, a kidney dialysis method, a blood oxygenation method, a blood salvage process disclosed in U.S. Pat. No. 5,971,948, a delipidation process disclosed in U.S. Pat. No. 5,484,396, a solvent extraction process disclosed in U.S. Pat. No. RE37, 584, a photoradiation process disclosed in U.S. Pat. No. 6,548,241, and the like. This EPRS may be applicable to cell-free plasma or white blood cells containing plasma, followed by removal of treated white blood cells before reinfusion into a patient.

In some aspects of the disclosure, the process comprises: (1) to separate plasma from the blood (or other body fluid) through a separation device (for example, a DC2000 separation apparatus as disclosed in U.S. Pat. No. 6,423,023, Cobe Spectra apparatus from Gambro BCT, Auto C apparatus from Baxter, etc.), (2) inactivate the pathogen (HBV, HCV, HIV, etc.) with known anti-pathogen agents (antibodies, complement, PRT, UV, drugs that can neutralize or inhibit cell binding, ligand binding, receptor blocking agents, etc.), and (3) then re-circulate the plasma back into the human body. The device to carry out this process can be linked with other applications, such as an extracorporeal liver assist system, a dialysis system, or other extracorporeal system.

Figure 9:
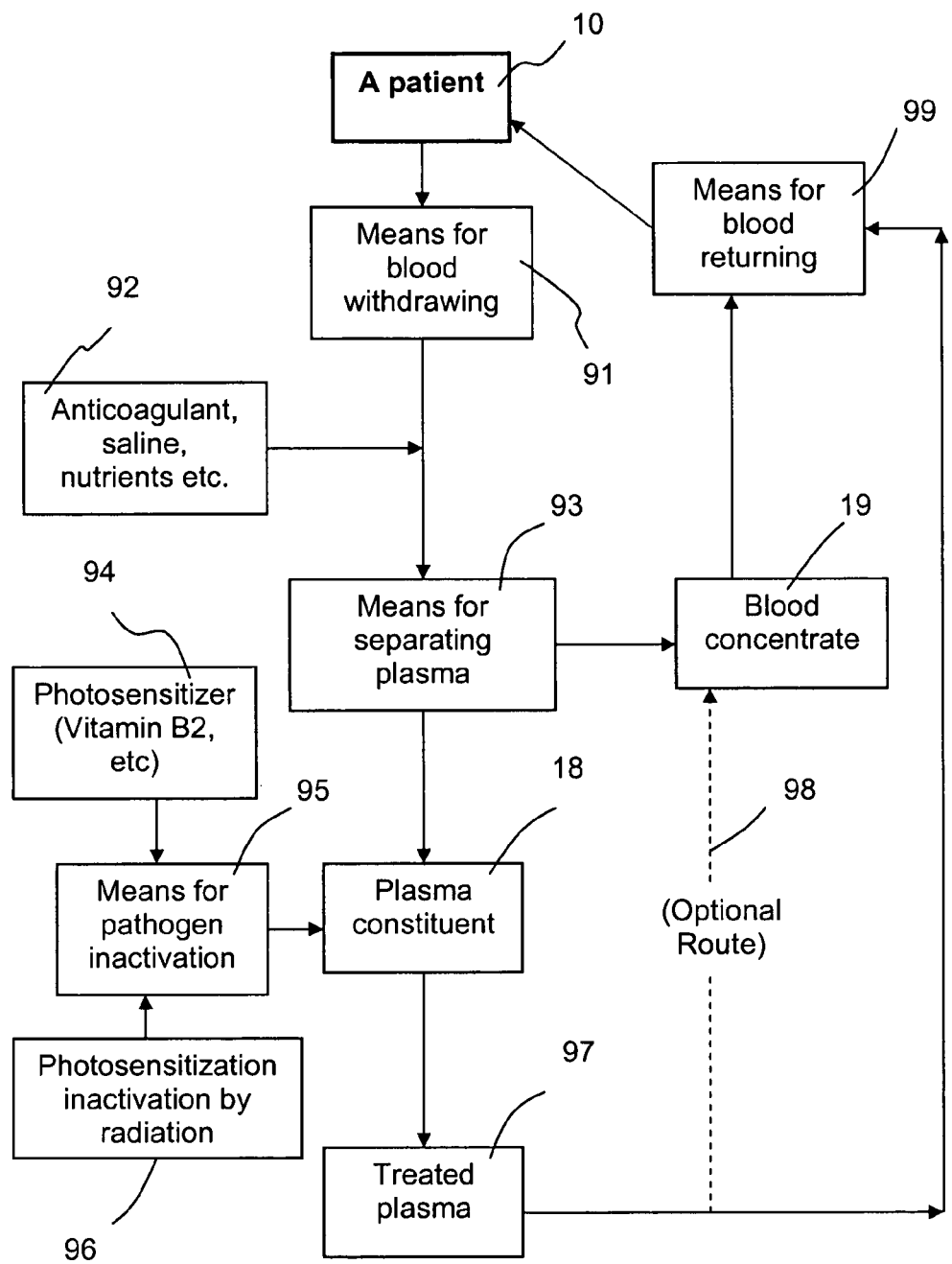
FIG. 9 is a schematic diagram of the separation and treatment system for an extracorporeal pathogen reduction or inactivation system.

FIG. 9 shows a schematic diagram of the separation and treatment system for an extracorporeal pathogen reduction or inactivation system. The extracorporeal pathogen reduction system comprises: (a) means 91 for withdrawing blood from a patient 10; (b) means 93 for separating a plasma constituent 18 from the blood; (c) means 95 for inactivating pathogen in the plasma constituent 18; and means 99 for returning treated plasma constituent 97 to the patient 10. Herein, the system may also apply to treating blood supply from a donor without the immediate steps of blood withdrawing or blood reinfusion. In one embodiment, supplemental fluid 92 such as anticoagulant, saline, and/or nutrients may be appropriately added to the system at any appropriate point of the system. In another embodiment, the means for inactivating the pathogen comprises adding at least one photosensitizer 94 into the plasma constituent 18 and providing photosensitized inactivation 96 at an effective amount of radiation, wherein the photosensitizer is riboflavin or selected from a group consisting of vitamin K1, vitamin K2, vitamin K5, vitamin K6, vitamin K7, vitamin K-S(II), vitamin L, and alloxazine compounds. In still another embodiment, the effective amount of radiation is at least 1 Joule per ml of plasma constituent for a period at least 1 second of radiation time. An optional route 98 for returning the treated plasma to the patient 10 is to mix with the blood concentrate 19.

In some aspects of the disclosure, the device may comprise three parts: (1) a separation device: a separation device is used to separate plasma (or nucleated-cell free fluid) from blood, for example, a DC2000 separation apparatus as disclosed in U.S. Pat. No. 6,423,023 or a co-pending application U.S. Ser. No. 10/195,814, (2) a treatment device: a device consists of a small entry port for adding anti-infective compounds and a treatment channel (tubing, hollow fibers, pouches, etc.) that can control the flow rate, mixing with material that can pass through the light and/or radiation, and (3) a return back to body device: a link where the cellular body fluid can return to the body without leaking or flush back. The device can link to other treatment device (for example, an extracorporeal liver assist system) where the other treatment is needed. The cell free body fluid of the disclosure includes plasma, abdominal cavity fluid and lymphoid fluid.

The separation method exploited herein comprises filtration that is characterized by filter membrane separation based on particle sizes, membrane materials of polycarbonate, nylon, polysulfone, polyimide, pore size of membrane at 0.1 to less than 1 μm for plasma collection, and a device of membrane, hollow fiber, tubing etc. Further, another separation method is by centrifugation separation based on the particle density and particle sizes. Typically, the enabling plasma separation system may include, but not limited to CS3000 by Baxter (centrifuge), Auto C by Baxter (filtration with centrifuge-type spinning membrane), PCS P2 by Heamonetics (centrifuge), Cobra Spectra (centrifuge), and DC2000 (filtration with orbital oscillation movement).

In one aspect of the invention, the blood-born pathogens comprise viruses (for example, HBV, HCV, HAV, HIV-1, HIV-2, HHV-6, HSV-1, HSV-2, CMV, EBV, rotavirus, adenoviruses, respiratory syncytial virus, parvovirus B19, Ebola virus, Varicella-zoster virus, poliovirus, Dengue virus, *Haemophilus influenza,* measles virus, mumps virus, Influenza viruses and the like); fungi (for example *aspergillus* spp, *candida* spp, and the like); bacteria (for example, *Pseudomonas aerogenosa, Clamydia pneumoniae, Mycobacterium tuberculosis* and the like).

In another aspectof the invention, the pathogen reducing or inactivating agent is selected from a group consisting of (1) Pathogen-specific antibodies (human IVIG, monoclonal antibodies, mouse monoclonal antibodies: humanized monoclonal antibodies, genetic engineered antibodies), (2) Complements, (3) Radiations, (4) ultraviolet (UV), (5) Pathogen Reduction Technology (as disclosed in U.S. Pat. No. 6,548,241), (6) Anti-infective drugs, such as anti-HIV-1 drugs, anti-HBV drugs, anti-HCV drugs, anti-fungi drugs, antibiotics, (7) Interferons, (8) Cytokines, and (9) Agents block pathogens from binding to the target cells such as amatadine, interferon, etc.

In still another aspect of the invention, the treatment target comprises patients infected with any pathogens, patients with chronic liver cirrhoses due to HBV infection, HIV-1 patients, HCV patients, mad cow disease patients, cleansing/preventive purposes that inactivate any unknown pathogens to protect any unwanted pathogens.

Photosensitizers which attack nucleic acids are known to the art. U.S. Pat. No. 5,342,752 issued Aug. 30, 1994 discloses the use of compounds based on acridine dyes to reduce parasitic contamination in blood matter comprising red blood cells, platelets, and blood plasma protein fractions. These materials, although of fairly low toxicity, do have some toxicity e.g. to red blood cells. U.S. Pat. No. 5,798,238 to Goodrich, Jr., et al., discloses the use of quinolone and quinolone compounds for inactivation of viral and bacterial contaminants. Riboflavin (7,8-dimethyl-10-ribityl isoalloxazine) has been reported to attack nucleic acids. Photoalteration of nucleic acid in the presence of riboflavin is discussed in Tsugita, A, et al. (1965), "Photosensitized inactivation of ribonucleic acids in the presence of riboflavin," Biochimica et Biophysica Acta 103:360–363; and Speck, W. T. et al. (1976), "Further Observations on the Photooxidation of DNA in the Presence of Riboflavin," Biochimica et Biophysica Acta 435:39–44. Binding of lumiflavin (7,8,10-trimethylisoalloxazine) to DNA is discussed in Kuratomi, K., et al. (1977), "Studies on the Interactions between DNA and Flavins," Biochimica et Biophysica Acta 476:207–217.

The photosensitizers useful in this invention include any photosensitizers known to the art to be useful for inactivating microorganisms. A "photosensitizer" is defined as any compound which absorbs radiation of one or more defined wavelengths and subsequently utilizes the absorbed energy to carry out a chemical process. Examples of such photosensitizers include porphyrins, psoralens, dyes such as neutral red, methylene blue, acridine, toluidines, flavine (acriflavine hydrochloride) and phenothiazine derivatives, coumarins, quinolones, quinones, and anthroquinones. Other photosensitizers are also useful in this invention, such as those using singlet oxygen-dependent mechanisms. Most preferred are endogenous photosensitizers. The term "endogenous" means naturally found in a human or mammalian body, either as a result of synthesis by the body or because of ingestion as an essential foodstuff (e.g. vitamins) or formation of metabolites and/or byproducts in vivo. Examples of such endogenous photosensitizers are alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (ravine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations. The term "alloxazine" includes isoalloxazines.

EXAMPLE NO. 1

Therapeutic Applications

An HIV-1 patient has HIV-1 viral loads of $10^7$ copies/mL and HCV viral loads of $10^6$ copies/mL. The patient is placed in the EPIS. This EPIS applies the PRT (Pathogen Reduction Technology) to inactivate known and unknown pathogens. The patient's blood was drawn from the left arm and filtered through a DC2000 device or other blood separation systems to separate the plasma from concentrated blood. The concentrated blood was re-circulated back to the body. The plasma is collected at a speed of 10 to 50 mL per minute. The plasma is directed into a plastic tubing and flow at a speed of 5 cm/min. A small entry port sits in the front end of the tubing can be opened to add anti-infectives. A small device creating a small turbulence when the plasma flows through it to create a mixing. The length of the tubing is configured and adjusted to accommodate the length of incubation time required. Once the treatment is complete, the plasma is returned back to the body. It was reported the viral loads in the plasma pouch can be reduced by 10,000 folds after 6 minutes (optimal period of time) of riboflavin/light treatment. The flow rate and volume processed can be adjusted to process a full body equivalent plasma volume in a reasonable time frame. It is expected to reduce 5–10 folds of virus per treatment cycle.

It is a lot better than any simple (stand alone) antiviral drug treatment in the market (Interferon treatment course: 6 months). Assuming the reduction is 10 folds, (because the device is in circulation. The rate can only be as good as the removal of toxic materials similar to the kidney dialysis machine) and the treatment is done every two days. This combination treatment is estimated to be able to reduce the viral load by 10,000-folds in 5–10 treatments. Although the kidney dialysis is not inexpensive, it is cheap and convenient than the standard anti-viral treatment.

The potential benefits of the current treatment system include: reduce the pathogens re-infection burden, reduce viral or other harmful microbial loads in blood, reduce the inflammation due to less infection, reduce time of treatment, reduce the cost, and improve the outcome quality (less damage, faster recovery).

Some aspects of the invention provide an extracorporeal pathogen reduction system comprising, in combination, means for withdrawing blood from a patient, means for separating a plasma constituent from the blood, means for inactivating pathogen in the plasma constituent, and means for returning treated plasma constituent to the patient. In one embodiment, the system further comprises an anticoagulant, nutrients or buffer solutions. In another embodiment, the means for inactivating the pathogen comprises adding at least one photosensitizer into the plasma constituent and providing photosensitized inactivation at an effective amount of radiation. The photosensitizer may comprise riboflavin, vitamin K1, vitamin K2, vitamin K5, vitamin K6, vitamin K7, vitamin K-S(II), vitamin L, and alloxazine compounds. In one preferred embodiment, the effective amount of radiation is at least 1 Joule per ml of plasma constituent for a period at least 1 second up to 10 minutes or longer of radiation time. In the case that the plasma component is spread in a thin layer, the effective amount of radiation is about a few Joules per $cm^2$ for riboflavin added solution.

From the foregoing description, it should now be appreciated that a combined system having an enhanced plasmapheresis chamber comprising a filter membrane and a plasma de-virusing (or de-infecting) means under a generally orbital motion that has optimal local shear forces and maximum quality flow output has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. An extracorporeal pathogen reduction system comprising:
    means for withdrawing blood from a patient;
    means for separating a plasma constituent from the blood, wherein the means for separating a plasma constituent from the blood comprises a blood filtration apparatus characterized by an orbital motion with filter membrane means, wherein said filtration apparatus comprises a chamber having a hollow interior enclosed by a first plate, a second plate, and a flexible seal element between the first plate and the second plate, wherein the first plate is either essentially parallel to or at on acute angle to the second plate so as to form a chamber gap for the hollow interior; means for directing blood into the chamber gap; a non-rotational drive structure; said second plate comprising the filter membrane means for separating plasma constituent from the blood, wherein the second plate is detachably coupled to said non-rotational drive structure that controls the second plate in an orbital motion in reference to a center axis of the first plate; a collecting means; means for directing the plasma constituent passing through said filter membrane means to said collecting means; and means for directing from the chamber gap a remaining constituent of the blood out of the chamber;
    means for inactivating pathogen in the plasma constituent; and
    means for returning treated plasma constituent to said patient.

2. The system of claim 1, wherein the means for inactivating the pathogen comprises adding at least one photosensitizer into the plasma constituent and providing photosensitized inactivation for inactivating pathogen at an effective amount of radiation.

3. The system of claim 2, wherein the photosensitizer is riboflavin.

4. The system of claim 2, wherein the photosensitizer is selected from a group consisting of vitamin K1, vitamin K2, vitamin K5, vitamin K6, vitamin K7, vitamin K-S(II), vitamin L, and alloxazine compounds.

5. The system of claim 2, wherein the effective amount of radiation is at least 1 Joule per ml of plasma constituent for a period at least 1 second of radiation time.

6. The system of claim 1, wherein the pathogen comprises *aspergillus* spp and *candida* spp.

7. The system of claim 1, wherein the pathogen is selected from a group consisting of *Pseudomonas aerogenosa, Clamydia pneumoniae,* and *Mycobacterium tuberculosis.*

8. The system of claim 1, wherein the pathogen is selected from a group consisting of HCV, HAV, HIV-1, HIV-2, HHV-6, HSV-1, HSV-2, CMV, EBV, rotavirus, adenoviruses, respiratory syncytial virus, parvovirus B19, Ebola virus, Varicella-zoster virus, poliovirus, Dengue virus, *Haemophilus influenza*, measles virus, mumps virus, and influenza viruses.

9. The system of claim 1, further comprising an anticoagulant.

10. A method of extracorporeally reducing pathogen burden of a patient comprising: filtering the patient's blood through a blood filtration apparatus configured for separating a plasma constituent from the blood; passing the plasma constituent through pathogen-reduction means for reducing the pathogen burden in the plasma constituent; and returning cellular components of the patient's blood back to said patient, wherein the filtering step is carried out with the blood filtration apparatus comprising a chamber having a hollow interior enclosed by a first plate, a second plate, and a flexible seal element between the first plate and the second plate, wherein the first plate is either essentially parallel to or at an acute angle to the second plate so as to form a chamber gap for the hollow interior; means for directing blood into the chamber gap; a non-rotational drive structure; said second plate comprising the filter membrane means for separating plasma constituent from the blood, wherein the second plate is detachably coupled to said non-rotational drive structure that controls the second plate in an orbital motion in reference to a center axis of the first plate; a collecting means; means for directing the plasma constituent passing through said filter membrane means to said collecting means; and means for directing from the chamber gap a remaining constituent of the blood out of the chamber.

11. The method of claim 10, wherein the pathogen-reduction means comprises at least one photosensitizer being added into the plasma constituent and a step of photosensitized inactivation with an effective amount of radiation to the plasma constituent.

12. The method of claim 11, wherein the photosensitizer is selected from a group consisting of vitamin B2, vitamin K1, vitamin K2, vitamin K5, vitamin K6, vitamin K7, vitamin K-S(II), vitamin L, and alloxazine compounds.

13. The method of claim 11, wherein the effective amount of radiation is at least 1 Joule per ml of plasma constituent for a period at least 1 second of radiation time.

14. The method of claim 10, wherein the pathogen-reduction means comprises an organic solvent being added into the plasma constituent in an amount and for a period of time sufficient to inactivate said pathogen, wherein the organic solvent is selected from a group consisting of ethers, alcohols, volatile chlorinated hydrocarbons, acetone and chloroform.

15. The method of claim 10, wherein the pathogen-reduction means comprises cyclodextrin being added into the plasma constituent in an amount and for a period of time sufficient to inactivate said pathogen, wherein the cyclodextrin is selected from a group consisting of an α-cyclodextrin, a β-cyclodextrin, a γ-cyclodextrin and a derivative thereof.

16. The method of claim 15, wherein the pathogen-reduction means further comprises cladribine being added into the plasma constituent in an amount and for a period of time sufficient to inactivate said pathogen.

17. The method of claim 10, wherein the pathogen is selected from a group consisting of HCV, HAV, HIV-1, HIV-2, HHV-6, HSV-1, HSV-2, CMV, EBV, rotavirus, adenoviruses, respiratory syncytial virus, parvovirus B19, Ebola virus, Varicefla-zoster virus, poliovirus, Dengue virus, *Haemophilus influenza*, measles virus, mumps virus, influenza viruses, *aspergillus* spp, *candida* spp, *Pseudomonas aerogenosa, Clamydia pneunaoniae*, and *Mycobacterium tuberculosis*.

* * * * *